United States Patent [19]

Watson et al.

[11] Patent Number: 5,998,159
[45] Date of Patent: Dec. 7, 1999

[54] METHODS FOR SCREENING FOR ANTIBIOTICS

[75] Inventors: Julia C. Watson, San Jose; Charles M. Moehle, Castro Valley; Ritu Gina Bahador, Dublin, all of Calif.; Victor James Hernandez, Williamsville, N.Y.

[73] Assignee: RiboGene, Inc., Hayward, Calif.

[21] Appl. No.: 09/021,184

[22] Filed: Feb. 10, 1998

Related U.S. Application Data

[60] Provisional application No. 60/037,534, Feb. 10, 1997.

[51] Int. Cl.$^6$ ............................... C12Q 1/02; C12Q 1/18
[52] U.S. Cl. ........................... 435/29; 435/32; 435/252.3
[58] Field of Search ............................. 435/29, 32, 252.3

[56] References Cited

PUBLICATIONS

An et al., 1979, "Cloning the spoT gene of *Escherichia coli*: identification of the spoT gene product", J. Bacteriol. 137:110–1110.
Baracchini, E. & Bremer, H., 1988, "Stringenet and growth control of rRNA synthesis in *Escherichia coli* are both medaited by ppGpp", J. Biol. Chem. 263:2597–2602.
Bremer & Ehrenberg, 1995, "Gaunosine tetraphosphate as a global regulator of bacterial RNA synthesis: a model involving RNA polymerase pausing and queuing", Biochimica et Biophysica pp. 15–36.
Broda, 1968, "Ribonucleic acid synthesis and glutamate excretion in *Escherichia coli*", J. Bacteriol., 96:1528–1534.
Cashel et al., 1996, *Escherichia coli and Salmonella Cellular and Molecular Biology*, ed. Neidhardt, F.C. ASM Press, Washington, D.C. pp. 1458–1496.
Cashel et al., 1994, "Detection of (p)ppGpp accumulation patterns in *Escherichia coli* mutants", *Methods in Molecular Genetics*, vol. 3, Molecular Microbiology Techniques, Part A. ed. Adolph, K.W. Academic Press, New York, pp. 341–356.
Cochran & Byrne, 1974, "isolation and Properties of a Ribosome–bound Factor Required for ppGpp Synthesis in *Escherichia coli*", J. Biol. Chem., 249:353–360.
Cole et al., 1987, "Feedback Regulation of rRNA Synthesis in *Escherichia coli*: Requirement for Initiation Factor IF2", J. Mol. Biol. 198:383–392.
Donachie, 1968, "Relationship between cell size and time of initiation of DNA replication", Nature 219:1077–1079.
Fehr & Richter, 1981, Stringent response of *Bacillus stearothermophilus*: evidence for the existence of two distinct guanosine 3', 5'–polyphosphate synthetase, J. Bacteriol. 145:68–73.
Fili et al., 1968, "A functional analysis of the rel gene in *Escherichia coli*", J. Mol. Biol. 45:195–203.
Fili & Freisen, 1969, "Isolation of "relaxed" mutants of *Escherichia coli*", J. Bacteriol. 95:729–731.
Freisen, J.D. et al., 1975, "Synthesis and Turnover of Basal Level Guanosine Tetraphosphate in *Escherichia coil*", J. Biol. Chem. 250:304–309.

Gaal & Gourse, 1990, Guanosien 3'–diphosphate 5'–diphosphate is not required for growth rate–dependent control of rRNA synthesis in *Escherichia coli*, PNAS USA 87:5533–5537.
Gentry & Cashel, 1996, "Mutational analysis of the *Escherichia coli* spoT gene identifies distinct but overlapping regions involved in ppGpp synthesis and degradation", Molecular Microbiol. 19(6):1373–1384.
Gentry & Cashel, 1995, "Cellular localization of the *Escherichia coli* SpoT protein", J. Bacteriol. 177:3890–3893.
Haseltine & Block, 1973, "Synthesis of guanosine tetra–and pentaphosphate requires th epresence of a codon–specific, uncharged transfer ribonucleic acid in the acceptor site of ribosomes", PNAS USA 70:1564–1568.
Heinemeyer et al., 1978, "Degradation of guanosine 3'–diphosphate 5'–diphosphate in vitro by the spoT gene product of *Escherichia coli*", Eur. J. Biochem. 89:125–131.
Heinemeyer & Richter, 1977, "In vitro degradation of guanosine tetraphosphate (ppGpp) by the enzyme associated with the ribosomal fraction from *Escherichia coli*", FEBS Lett. 84:357–361.
Heinemeyer & Richter, 1978, "Mechanism of the in vitro breakdown of guanosine 5'–diphosphate 3'–diphosphate in *Escherichia coli*", PNAS USA 75:4180–4183.
Hernàndez & Bremer, 1990, "Guanosine Tetraphosphate (ppGpp) Dependence of the Growth Rate Control of rrnB P1 Promoter Activity in *Escherichia coli*", J. Biol. Chem. 265:11605–11614.
Hernàndez & Bremer, 1993, "Characterization of RNA and DNA synthesis in *Escherichia coli* strains devoid of ppGpp", J. Biol. Chem. 268:10851–10862.
Hern``ndez & Bremer, 1991, "*Escherichia coli* ppGpp Synthetase II Activity Requires spoT", J. Biol. Chem. 266(6):5991–5999.
Jinks–Robertson & Nomura, 1987, "Ribosomes and tRNA", in *Escherichia coli and Salmonella Cellular and Molecular Biology*, ed. Neidhardt, F.C., ASM Press, Washington, D.C. pp. 1358–1385.

(List continued on next page.)

*Primary Examiner*—Johnny F. Railey, II
*Attorney, Agent, or Firm*—Pennie & Edmonds LLP

[57] ABSTRACT

The present invention provides methods for identification of antibiotic agents which cause the accumulation of ppGpp in bacterial organisms involving a relA-independent pathway. The methods comprise screening assays in which test compounds are brought into contact with relA$^-$ test cells and observing the effect such compounds have on ppGpp levels in the test cells. The invention also provides genetically manipulated relA$^-$ test cells which contain a reporter gene the expression of which is sensitive to the level of ppGpp. The invention also encompasses agents identified by the screening assays, and uses of these agents in the treatment of infectious diseases.

26 Claims, No Drawings

OTHER PUBLICATIONS

Johnson et al., 1979, "Role of the spoT Gene Product and Manganese Ion in the Metabolism of Guanosine 5'–Diosphate 3'–Diphosphate in *Escherichia coli*", J. Biol. Chem. 254:5483–5487.

Laffler & Galant, 1974, "spoT, a new genetic locus involved in the stringent repsonse in E. coli", Cell 1:27–30.

Little et al., 1983, "rpo mutation in *Escherichia coli* alters control of ribosome synthesis by guanosine tetraphosphate", J. Bacteriol. 154:787–792.

Little et al., 1983, Physiological characterization of *Escherichia coli* rpoB mutants with abnormal control of ribosome synthesis, J. Bacteriol. 155:1162–1170.

Mechold et al., 1996, "Functional Analysis of a relA/spoT Gene Homolog from *Steptococcus equisimilis*", J. Bacteriol. 178:1401–1411.

Metzger et al., 1989, "Protein sequences encoded by the relA and the spoT genes of *Escherichia coli* are interrelated", J. Biol. Chem. 264:9122–9125.

Munro et al., 1995, "Influence of the RpoS (KatF) Sigma Factor on Maintenance of Viability and Culturability of *Escherichia coli* and *Salmonella typhimurium* in Seawater", Applied and Environ. Microbiol. 61(5):1853–1858.

Murray & Bremer, 1996, "Control of spoT–dependent ppGpp Synthesis and Degradation in *Escherichia coli*", J. Mol. Biol. 259:41–57.

Pao and Gallant, 1978, "A Gene Involved in the Metabolic Control of ppGpp Synthesis", Mol Gen. Genet. 158:271–277.

Pedersen & Kjeldgaard, 1977, "Analysis of the relA gene product of *Escherichia coli*", Eur. J. Biochem. 76:91–97.

Reddy et al., 1995, "Evidence for a ppGpp–binding Site on *Escherichia coli* RNA Polymerase: Proximity Relationship with the Rifampicin–binding domain", Mol Microbiol. 15:255–265.

Richter et al., 1979, "The guanosine 3',5'–bis(diphosphate)(ppGpp) cycle", Eur. J. Biochem. 99:57–64.

Richter et al., 1980, "Uncharged tRNA Inhibits Guanosine 3',5'–Bis (Diphosphate) 3'–Pyrophosphohydrolase [ppGppase], the spoT Gene Product from *Escherichia coli*", Molec. Gen. Genet. 178:325–327.

Rudd et al., 1985, "Mutations in the spoT gene of *Salmonella typhimurium*: effects on *his* operon expression", J. Bacteriol. 163:534–542.

Ryals et al., 1982, "Control of rRNA and tRNA synthesis in *Escherichia coli* by guanosine tetraphosphate", J. Bacteriol. 151:1261–1268.

Ryals et al., 1982, "Control of RNA synthesis in *Escherichia coli* after a shift to higher temperature", J. Bacteriol. 151:1425–1432.

Sarubbi et al., 1989, "Characterization of the spoT Gene of *Escherichia coli*", J. Biol. Chem. 264:15074–15082.

Sarubbi et al., 1988, "Basal ppGpp Level Adjustment Shown by New spoT Mutants Affect Steady State Growth Rates and rrnA Ribosomal Promoter Regulation in *Escherichia coli*", Mol Gen. Genet. 213:214–222.

Schlessinger and Schaecter, 1989, *Mechanisms of Microbial Disease*, ed. Schaechter, M., Williams & Wilkins, Baltimore, pp. 20–30.

Schreiber et al., 1991, "Overexpression of the relA Gene in *Escherichia coli*", J. Biol Chem. 266:3760.

Silverman & Atherly, 1979, "The search for guanosine tetraphosphate (ppGpp) and other unusual nucleotides in eucaryotes", Microbiol. Rev. 43:27–41.

Stephens et al., 1975, "Guanosine 5'–diphosphate 3'–diphosphate (ppGpp): positive effector for histidine operon transcription and general signal for amino–acid deficiency", PNAS USA 72:4389–4393.

Sundar & Chang, 1992, "The role of guanosine–3',5'–bis–pyrophosphate in mediating antimircrobial activity of the antibiotic 3,5–dihydroxy–4–ethyl–trans–stilbene", Antimicrob. Agents Chemother. 36:2645–2651.

Sy, 1977, "In vitro degradation of guanosine 5'–diphosphate, 3'–diphosphate", PNAS USA 74:5529–5533.

Sy & Akers, 1976, "Purification and Properties of Guanosine 5'–3'–Polyphosphate from *Bacillus brevis*", Biochemistry 15:4399–4393.

Xiao et al., 1991, "Residual Guanosine 3',5'–Bispyrophosphate Syntheitic Activity of relA Null Mutants Can be Eliminated by spoT Null Mutations", J. Biol. Chem. 266(9):5980–5990.

Zhang & Bremer, 1995, "Control of the *Escherichia coli* rrnB P1 promoter strength by ppGpp", J. Biol. Chem. 370:11181–11189.

METHODS FOR SCREENING FOR ANTIBIOTICS

This patent application claims the benefit under 35 U.S.C. §119(c) of U.S. provisional application Ser. No. 60/037,534, filed Feb. 10, 1997, which is incorporated by reference herein in its entirety.

1. INTRODUCTION

The present invention relates to methods for high-throughput screening for compounds with antibiotic activity. Specifically, the invention relates to high-throughput screens which target mechanisms for accumulation of the nucleotide guanosine-3',5'bis-pyrophosphate ("ppGpp") by relA$^+$ independent pathways in bacteria. Such targets include ppGpp synthetase II (PSII) and ppGpp degradase (SpoT), both encoded by the spoT locus in bacteria. The invention further relates to novel compounds identified using such screening methods.

2. BACKGROUND

Resistance to currently available antibiotics has created a need for new antibiotic agents. In the United States alone, 19,000 hospital patients die each year due to nosocomial (hospital-acquired) bacterial infections (Service, R., 1995, Science 270:724–727). These infections, caused by organisms such as *Staphylococcus aureus, Pseudomonas aeruginosa, Enterococcus faecium* and *Enterococcus faecalis*, have become increasingly resistant to currently approved antibiotics. For example, significant clinical problems include methicillin-resistant strains of *S. aureus*, which are resistant to all current antibiotics except vancomycin (a drug of last resort because of severe side effects), and a vancomycin-resistant strain of *E. faecium* enterococci which is now found world-wide. The occurrence of vancomycin-resistant enterococci isolated from nosocomial infections rose from 0.4% to 13.6% in the relatively short time span from 1989 to 1993 (Tenover, F. C. and Hughes, J. M., 1996, JAMA 275(4):300–304) (reporting statistics from the Centers for Disease Control and Prevention). Even community-acquired organisms such as *Streptococcus pneumoniae* are increasingly resistant to antimicrobial agents, with a significant number of isolates being resistant to penicillin and extended-spectrum cephalosporins. Id.

The emergence and spread of resistant bacterial organisms are primarily caused by acquisition of drug resistance genes, resulting in a broad spectrum of antibiotic resistance (e.g., extended-spectrum cephalosporin-resistant mutant β-lactamases found in several bacterial organisms). Genetic exchange of multiple-resistance genes, by transformation, transduction and conjugation; combined with selective pressures in settings such as hospitals where there is heavy use of antibiotic therapies, enhance the survival and proliferation of antimicrobial agent-resistant bacterial strains occurring by, e.g., spontaneous mutants. Id. Although the extent to which bacteria develop resistance to antimicrobial drugs and the speed with which they do so vary with different types of drugs, resistance has inevitably developed to all antimicrobial agents (Gold and Moellering, Jr., 1996, New Eng. J. Med., 335(19):1445–1453).

To prevent or delay the buildup of a resistant pathogen population, different chemicals that are effective against a particular disease-causing bacterium must be available. Thus, there is a need to develop methods for identifying compounds which can penetrate and specifically kill the pathogenic bacterial cell, or arrest its growth without also adversely affecting its human, animal, or plant host.

2.1. CURRENT SCREENING METHODS

Because resistance to antibiotics is assuming even greater clinical importance, there is a pressing need to develop more effective methods for antibiotic drug discovery. Traditional approaches to screening for antimicrobial agents include chemical modification of existing drugs and mass screening of compounds for bacterial growth inhibition. The first approach, chemical modification of existing antibiotics, attempts to circumvent bacterial resistance while finding more potent activities. This approach has shown some success, however, it does not produce new classes of drugs and is unlikely to identify new bacterial processes as targets for drug intervention. The second is to directly test compounds for their ability to inhibit bacterial growth using standard microbiological methods, such as growth inhibition assays where libraries of natural products, semisynthetic, or synthetic chemicals are screened for their ability to kill or arrest growth of the target pathogen or a related nonpathogenic model organism. These tests are useful in that they are fast, uncomplicated, relatively inexpensive and allow for rapid testing of large libraries of compounds. However, such screens are blind to the compound's mechanism of action so that rate of efficacy, selectivity, and resistance remain elusive. That is, the promising lead compounds that emerge from such screens must not only be tested for possible toxicity to the human, animal, or plant host, they also undergo detailed mechanism-of-action studies conducted to identify the affected molecular target and precisely how the drug interacts with this target.

Another approach involves screening for compounds which target the resistance mechanism of known antibiotics. The compounds are then administered in conjunction with known antimicrobial agents. This technique is currently being tested for treating organisms resistant to tetracycline compounds. Tetracycline resistant organisms do not accumulate tetracycline within the cell and actually excrete the drug by cellular efflux pumps. Compounds which are tetracycline analogs that tightly bind to the pumps are given in conjunction with tetracycline to assist tetracycline in reaching its target in the bacterial cell (Service, 1995, Science 270:724–727), supra. This approach, however, is complicated and does not affect the underlying resistance mechanism.

2.2. DECIPHERING MECHANISMS OF ANTIBIOTIC ACTION

Once antibiotics are identified, a number of studies can be performed to determine their mechanism of action and their selectivity. Such analyses can sometimes provide new understanding of basic cellular mechanisms.

For example, sulfonamides (or sulfa drugs), the first important antimicrobial agents identified, are actually antimetabolites and riot antibiotics. Sulfanilamide, one of the sulfonamide class drugs, is a structural analog of para-aminobenzoic acid ("PABA"). The mode of action of sulfanilamide was unknown until it was discovered that PABA is required for the synthesis of the essential vitamin, folic acid. Folic acid synthesis is required for bacterial growth since bacteria are not capable of folic acid uptake. Sulfonamides inhibit the bacterial synthesis of folic acid by acting as competitive inhibitors of PABA. For humans, folic acid is also an essential vitamin, but unlike bacteria, humans are capable of uptake of folic acid and can obtain the vitamin through diet. As a result, bacteria, but not humans, are vulnerable to sulfa drugs which inhibit folic acid synthesis. In the sulfa class alone, thousands of chemically modified derivatives have been studied with about 25 of them still in use.

Similarly, much has been learned about peptidoglycan synthesis since the discovery of the penicillin and cephalosporins (peptidoglycan is the critical component in maintaining the shape and rigidity of both Gram positive and Gram negative bacterial organisms). Therefore the discovery of new classes of drugs can broaden the general understanding of bacterial physiology as well as provide for new antibacterial chemotherapeutics.

2.3. THE USE OF ANTIBIOTICS TO STUDY THE METABOLISM OF ppGpp

Guanosine-3',5'bis-pyrophosphate or guanosine tetraphosphate (ppGpp) is a nucleotide which inhibits bacterial growth when it accumulates intracellularly. In the enteric bacterium *Escherichia coli*, there are two enzymes which catalyze the synthesis of ppGpp. One of the enzymes is ppGpp synthetase I (PSI) and is encoded by the relA locus. The PSI enzyme is activated during amino acid starvation which results in what is known as the stringent response (Cashel, 1969, J. Biol. Chem. 244:3133–3141; Cashel and Gallant, 1969, Nature 221:838–841). Although the stringent response was first characterized as a response to amino acid starvation, it is now recognized that ppGpp levels change in response to a variety of stress conditions, including carbon, nitrogen or phosphate starvation, heat shock, osmotic shock and pH changes (Murray and Bremer, 1996, J. Mol. Biol. 259:41–57; Cashel et al., 1996, *Escherichia coli* and Salmonella Cellular and Molecular Biology, ed. Neidhardt, F.C. ASM Press, Washington, D.C. pp. 1458–1496). The second ppGpp synthetic enzyme is ppGpp synthetase II (PSII), and is encoded by the spoT Locus.

Certain compounds, including several antibiotics, have been used as tools to study the metabolism of ppGpp in bacteria. For example, Cortay & Cozzone (Cortay & Cozzone, 1983, Biochimica et Biophysica Acta, 755:467–473) used polymyxin B and gramicidin, antibiotics which disrupt the cell membrane and thereby exert an antibacterial effect, to study ppGpp since a secondary effect of these antibiotics is a decrease in the rate of ppGpp degradation. The assays used by Cortay and Cozzone to study the metabolism of ppGpp involved measuring the intracellular levels of nucleotides following drug treatment or amino-acid starvation of bacteria. As a general screening method, such an approach would be time consuming and better suited to studying the metabolic effect of individual agents.

The effects of various antibiotics which interfere with protein synthesis were also investigated for effects on ppGpp degradation. Tetracycline, chlortetracycline and thiostrepton were shown to strongly inhibit ppGpp degradation in vitro, and levallorphan (a morphine analogue) moderately inhibited ppGpp degradation in vitro (Richter, 1980, Arch. Microbiol. 124:225–332).

However, many of these results obtained in vitro have little bearing in vivo where direct contact of the degradase with the unmetabolized antibiotic may not occur. In the case of tetracycline, the inhibition was ascribed to chelation of manganese at high concentrations of the antibiotic. The concentrations required would not be achievable in vivo.

An antibiotic produced by *Xenorhabdus luminescens*, 3,5-dihydroxy-4-ethyl-trans-stilbene ("ES"), is thought to inhibit bacterial cell growth via an increase in ppGpp concentration by the relA$^+$-dependent mechanism (Sundar & Chang, 1992, Antimicrobial Agents and Chemotherapy 36(12):2645–2651). Sundar & Chang reported that ES inhibited growth of a stringent *E. colis* (relA+), but did not inhibit growth of an isogenic relaxed strain (relA–). In addition, ES caused ppGpp to accumulate in a relA+ strain but not in relA–-strain. Furthermore, ES did not appreciably interfere with ppGpp degradase. Together these properties strongly suggested that ES action is to induce relA-dependent ppGpp synthesis, which leads to inhibition of growth.

3. SUMMARY OF THE INVENTION

The invention relates to high-throughput screens which target ppGpp accumulation in bacterial organisms by relA$^+$ (PSI) independent pathways. Such targets include, for example and not by way of limitation, ppGpp synthetase II (PSII) and 3'-pyrophosphohydrolase, ("ppGpp degradase") both of which are encoded by the spoT locus. The ppGpp degradase enzyme is also referred to as the spoT enzyme, "ppGpp hydrolase", and "ppGppase" in the literature.

The invention is based, in part, on applicants' recognition that compounds which cause ppGpp accumulation in a relA$^+$ (PSI) independent manner, such as by enhancing PSII activity or inhibiting ppGpp degradase, have the potential to be therapeutically beneficial as an antibiotic. This antibiotic property exists since increasing levels of ppGpp inhibit many cellular processes, including ribosomal RNA synthesis, and thus, ribosomes, which are essential for bacterial survival and growth. Deletion of the spoT gene, removes both PSII and ppGpp degradase and is not tolerated in the presence of a wildtype relA allele (Sarubbi et al., 1988, Mol. Gen. Genet., 213:214–222), suggesting that accumulation of ppGpp is lethal. Apparently, an adequate level of degradase in the organism is essential to prevent accumulation of toxic levels of ppGpp. Compounds which, for example, reduce, or inhibit this level of degradase activity are attractive candidates for therapeutic use. Similarly, compounds which enhance PSII activity are also desired. Accordingly, the invention provides methods for screening for potential antibiotic drugs by isolating compounds that, for example, enhance PSII ppGpp production or inhibit ppGpp degradase at the spoT locus in bacteria.

The screens of the invention use a bacterial strain lacking PSI activity due to a deletions or mutation in the relA gene (also known as "relaxed" strain) and having a wildtype spoT gene thus producing normal PSII activity and normal ppGpp degradase activity (PSII synthesizes ppGpp, but under different conditions than PSI). Alternatively, the screen could be performed in strains that have functional or wildtype RelA activity, but this activity is controlled and limited to levels that are acceptable and that allow accurate detection of ppGpp accumulation in the presence of active compounds.

The invention further comprises assays which utilize recombinant test cells which comprise a reporter gene under the control of a promoter which is either positively or negatively controlled by ppGpp. Chemicals tested which score positive for ppGpp accumulation and growth inhibition in this strain background will be independent of PSI, and thus unique from those previously isolated, such as ES (Sundar and Chang, 1992).

Bacterial strains without PSI activity (e.g., relA mutated strains) are advantageously used in the screens of the invention since this eliminates the potential for isolating compounds which causes ppGpp synthesis by the PSI enzyme and allows for the identification of compounds that specifically affect PSI-independent factors in ppGpp accumulation. This is significant since bacteria which lose the PSI gene by mutation are not uncommon and occur readily among laboratory isolates of *E. coli*. Elimination of PSI dependent synthesis, using relA mutant strains, allows for specific targeting of ppGpp degradase and/or PSII synthease.

Strains of *E. coli* with deletions in both the relA gene and the spoT gene have been obtained in the laboratory. These mutants have no functional ppGpp synthetase activity and do not have detectable intracellular ppGpp. These mutants are further characterized by slow growth, failure to divide normally and multiple amino acid auxotrpohies (Xiao et al., 1991, J. Biol. Chem 266:5980–5990). They are rapidly overgrown in mixed cultures with wildtype *E. coli* (V. J. Hernandez, personal communication) These observations suggest that the ppGpp signaling pathways provide some selective advantage to the bacterium and the genes encoding the balanced activities of synthetase and degradase are not readily deleted.

The above embodiment is illustrated by way of working examples which provide screens for compounds which either stimulate PSII or inhibit degradase, using a bacterial strain with a defective PSI gene, and growing the strain on a medium which is typically unsuitable for growth of the strain except in the presence of a compound that causes an increase in ppGpp levels.

In another embodiment, ppGpp accumulation caused by compounds which, for example, inhibit ppGpp degradase or, alternatively, enhance PSII activity, are screened using a bacterial strain with a defective PSI gene, which contains a reporter gene responsive to changes in the intracellular concentration of ppGpp.

In a less preferred embodiment, the assay strain has a functional relA gene.

A biochemical assay may be used to verify that the compounds which provide positive results in the physioclogical assays described above increase intracellular levels of ppGpp. Compounds which score positive in the first assay can be added to growing cells which are labeled with $^{32}P$ or $^{33}P$ orthophosphate. A change in intracellular levels of ppGpp is then assayed by extracting and separating labeled nucleotides, including ATP, GTP, ppGpp and pppGpp e.g., using thin layer chromatography (TLC) and visualization by autoradiography. Since this additional assay allows accurate detection of increases in intracellular levels of ppGpp, it will establish whether promising compounds are true modulators of intracellular ppGpp levels. The separation techniques which can be used are well known in the art. For example, one useful TLC method is described in M. Cashel, 1994, Methods in Molecular Genetics, vol. 3, Molecular Microbiology Techniques, Part A, ed. Adolph, K. W. (Academic Press, New York) pp. 341–356) and is incorporated by reference in its entirety.

Similarly, labeling and visualization methods could be used, as are well known in the art, such as radioactive or other isotopes incorporated into orthophosphate, guanosine or other precursors of ppGpp, combined with autoradiography, mass-spectrometry or other appropriate methods of detection.

In another embodiment, purified or partially purified SpoT protein can be used in an enzymatic assay to confirm that compounds identified in the primary assay inhibit the degradation of ppGpp. Purified or partially purified SpoT is combined with ppGpp or pppGpp in the presence and absence of test compounds. Degradase activity is measured by formation of the products pyrophosphate and GTP or GDP. These products can be detected by quantitation of radioactivity if the substrates are radiolabeled, by quantitation of pyrophosphate or by other methods known in the art.

In another embodiment, the invention relates to novel compounds identified by using such screening methods, as well as the uses of these compounds for developing antibiotic drugs for treatment of infectious diseases in animals.

The benefits of the approach taken in the present invention include its relative speed, cost, and the ability to rapidly test large numbers of compounds. Significantly, in contrast to simple growth inhibition screens, the targeted screening of the invention seeks to restrict drug discovery to compounds that act by specific mechanisms. The assays have been carefully designed to target an essential bacterial process that is not found in mammalian cells. Mammalian cells do not regulate transcription or translation via the ppGpp pathway (Silverman et al., 1979, Microbiol. Rev. 43:27–41). Therefore, compounds which affect the ppGpp pathway have the potential to be both very effective in controlling bacterial growth while causing less side effects to the infected host.

The methods of the present invention provide an efficient, focused approach to drug discovery with significant improvements over previous methods. One major improvement is a method for increasing the efficiency of drug discovery by ensuring that lead compounds are more likely to affect their desired molecular target inside the test organism. Unlike the traditional approaches used for antimicrobial drug screening, which are either blind to the bacterial mechanism which is being targeted and/or do not provide for new classes of antibiotics, the present invention targets a unique bacterial process. The screening methods described herein can identify compounds that cause ppGpp accumulation by relA independent mechanisms, such as, enhanced PSII activity or inhibition of ppGpp degradase. Using the present approach new classes of compounds may be found, and efficacy and selectivity of these compounds can be optimized.

4. DEFINITIONS ppGpp—either or both guanosine nucleotide analogs of GDP and GTP, bearing a pyrophosphate group esterified to the 3'-hydroxyl of the ribose moiety.

PSI—ppGpp synthase I which is encoded at the relA locus.

PSII—ppGpp synthase II which is not encoded at the relA locus.

relA$^+$ independent pathway(s)—biochemical pathway(s) of ppGpp
 synthesis or degradation not catalyzed by protein(s) encoded at the relA locus.

AT—3-amino-1,2,4-triazole in vitro—occurring outside a whole cell, such as in an reaction using purified components.

in vivo—occurring within a living organism, such as an assay using growth of whole bacterial cells.

5. DETAILED DESCRIPTION OF THE INVENTION

The present invention provides methods and compositions for identifying compounds that are capable of causing the accumulation of ppGpp in bacteria.

In one embodiment, the invention provides methods for the identification of compounds that enhance the activity of ppGpp synthase II (PSII). In another embodiment, the invention provides methods for the identification of compounds that inhibit the activity of ppGpp degradase. The methods comprise screening assays in which test compounds are brought into contact with test cells, and observing the effect such compounds have on ppGpp levels in the test cells.

In general, the methods of the invention involve contacting a test compound with relA deficient test cells for a time sufficient to allow the test compound to cause ppGpp accumulation, determining the level of ppGpp or the effect of ppGpp accumulation, and comparing the level or effect obtained to the level or effect in a test cell which has not been contacted with the test compound, such that if the level or effect of ppGpp in the cells contacted with the test compound is different from those cells not contacted, the test compound is identified as a potential candidate.

In a less preferred embodiment, relA$^+$ strains of test cells can also be used in the methods of the invention.

Instead of measuring directly the level of ppGpp in the test cells, the invention provides two strategies for detecting the accumulation of ppGpp efficiently. The first strategy is based on detecting paradoxical growth of test cells under stress conditions; such growth is affected by ppGpp level which regulates certain biosynthetic pathways. The other strategy employs a reporter gene the expression of which is under the control of a promoter that is either negatively or positively regulated by ppGpp. Methods based on these strategies can readily be automated and adapted for high throughput screening.

In another embodiment, the invention provides genetically manipulated relA$^-$ test cells which contain a reporter gene the expression of which is sensitive to the level of ppGpp. Both reporter mRNAs and reporter molecules in test cells can by design be easily detected and quantitated by techniques known in the art.

The term "test cell" as used herein referred to bacterial cells that are generally deficient at the relA locus or its equivalent (relA$^-$), and are preferably spoT$^+$. Generally, the test cells have been genetically manipulated for use in the screening assays of the invention. The term also encompasses any progeny of the subject test cell.

The term "ppGpp" is used in this invention to designate collectively either or both ppGpp (guanosine tetraphosphate) or pppGpp (guanosine pentaphosphate). The nucleotide pppGpp is converted to ppGpp in vivo by removal of the 5' terminal phosphate by the product of the gpp gene (pppGpp 5'-phosphohydrolase), and, most likely, to a lesser extent by the product of the ppx gene (exopolyphosphatase) (Koonin, 1994, Trends Biochem. Sci., 19:156–157; Kuroda et al. 1997, J. Biol. Chem. 272:21240–21243). The product of the spoT gene can degrade pppGpp or ppGpp to GTP or GDP, respectively, by removal of the 3'pyrophosphate. For the purposes of this invention, pppGpp and ppGpp are essentially interchangeable in their function as regulatory molecules, since accumulation of the former leads rapidly to accumulation of the latter.

The term "ppGpp accumulation" as used herein, refers to the accumulation of ppGpp or pppGpp inside test cells of the invention in which the synthesis or degradation is not catalysized by protein(s) encoded at the relA locus. Generally, ppGpp accumulation in test cells of the invention results from the activity of ppGpp synthase II (not ppGpp synthase I), and/or the relative lack of activity of ppGpp degradase. The activities of PSII and ppGpp degradase in test cells are targets in the screening assays of the invention.

The term "test compound" refers to a compound to be tested by one or more screening assays of the invention as a putative agent that causes ppGpp accumulation. The test compounds of the invention encompass numerous classes of chemical molecules, though typically they are organic molecules, and preferentially of low molecular weight. Typically, these compounds have a molecular weight of more than about 50, but less than about 3,000, and preferably less than 1,000.

Test compounds are obtained from a wide variety of sources including collections of natural products in the form of bacterial, fungal, plant and animal extracts; and synthetical chemical libraries. Numerous means known in the art are available for the random, directed and combinatorial synthesis of a wide variety of chemical structures. In addition, natural products or known antibiotic compounds may be subjected to random or directed chemical modifications to produce derivatives and structural analogs for use as test compounds in the invention. Usually various predetermined concentrations are used for screening such as 0.001 $\mu$M, 0.01 $\mu$M, 0.1 $\mu$M, 1.0 $\mu$M, 10 $\mu$M, and 100 $\mu$M.

Test compounds that score positive in the screening assays of the invention are putative agents that cause ppGpp accumulation, and are useful as leads for the development of therapeutic agents useful for the treatment of infectious diseases. Drugs based on such agents are likely to be both very effective in controlling growth in a broad spectrum of bacteria while causing minimal side effects to the treated subject.

The invention further provides biochemical assays which are used to further study the test compounds which produced positive results in the screening assays of the invention.

For clarity of discussion, the invention is described in the subsections below by way of example of E. coli. However, the principles may be applied to other bacteria which use similar mechanisms for regulation of intracellular ppGpp level.

5.1. REGULATION OF ppGpp

While not limited to any theory on how the level of ppGpp is regulated in bacteria, the methods of the invention are based in part on our understanding of the mechanisms involving ppGpp through which bacteria adapts to changes in the environment.

Bacteria generally exist in rapidly changing nutritional environments. To optimize growth and division in these various environments, bacteria developed sophisticated gene control mechanisms to allow the organism to produce particular enzymes in quantities that is optimal for the environment. Similarily, the translation apparatus itself is controlled by growth conditions.

For purposes of the treatment of human diseases caused by bacteria, understanding these gene control mechanisms provides an opportunity to look for compounds which adversely affect the bacterial genes that control growth. With this in mind, applicants have developed a strategy for screening for potential antibiotic drugs by identifying compounds which cause an accumulation of ppGpp via a relA independent pathway such as, for example, enhancing PSII activity or inhibiting ppGpp degradase. The assays of the invention provide a highly sensitive system that can be used to detect compounds that would otherwise be overlooked by ppGpp assays which have been used to study gene function in bacteria.

The genes encoding ribosomal RNA ("rRNA") respond rapidly to changes in the environment or in the growth medium. A reduction of rRNA synthesis in response to amino acid starvation is known as the "stringent response." During amino acid starvation, it is advantageous to down-regulate rRNA synthesis since the need for ribosomes is reduced when one of their substrates, i.e., amino acids, is in limited supply.

ppGpp appears to be responsible for negative regulation of rRNA synthesis during the stringent response. In *E. coli*, the PSI enzyme encoded at the relA is activated during amino acid starvation. The PSI enzyme is located on the ribosome and is activated by codon-specific binding of uncharged tRNA in the ribosomal RNA acceptor site (Haseltine and Block, 1973, Proc,. Natl. Acad. Sci. USA 70:1564–1568; Cochran and Byrne, 1974, J. Biol. Chem. 249:353–360; Pedersen and Kjeldgaard, 1977, Eur. J. Biochem 76:91–97).

During amino acid starvation, it is advantageous to down-regulate rRNA synthesis since the need for ribosomes is reduced when one of their substrates, i.e., amino acids, is in limited supply. In contrast, synthesis of amino acids must be up-regulated to overcome the starvation condition. This regulatory scheme assures that cellular energy is not wasted on de novo biosynthesis when amino acids are available in the growth medium, or on ribosome synthesis when amino acid supplies are exhausted.

Although the stringent response was first characterized as a response to amino acid starvation, it is now recognized that ppGpp levels change in response to a variety of other stress conditions, including carbon, nitrogen or phosphate starvation, heat shock, osmotic shock and pH changes (Murray and Bremer, 1996, J. Mol. Biol. 259:41–57; Cashel et al., 1996, *Escherichia coli* and Salmonella Cellular and Molecular Biology, ed. Neidhardt, F.C. ASM Press, Washington, D.C. pp. 1458–1496). Although the stringent response was first described in *E. coli*, it is known to be a general stress response and ppGpp has been found in all eubacteria tested (M. Cashel, 1994, Methods in Molecular Genetics, vol. 3, Molecular Microbiology Techniques, Part A, ed. Adolph, K. W. (Academic Press, New York) pp. 341–356)).

The relA structural gene consists of 743 codons encoding a protein of about 84 kDa. The relA gene product has two domains, one for ribosomal binding and the other for ppGpp synthetic activity (Schreiber et al., 1991, J. Biol. Chem. 266:3760). The relA gene or its equivalent in other bacteria is expected to share a high degree of sequence homology with the relA gene of *E. coli*. Such a gene in other bacteria may be identified by techniques commonly known in the art, such as hybridization assays using the relA gene as a probe.

RelA mutants, or relaxed mutants, are well characterized. A large number of relaxed mutants with RNA accumulation behavior ranging from slightly to strongly relaxed were isolated and characterized by Fiil and Friesen, 1968, J. Mol. Biol. 45:195–203; Fiil and Friesen, 1969, J. Bacteriol. 95:729–731. Relaxed mutants have increased permeability to glutamate (Broda, 1968, *Escherichia coli*. J. Bacteriol. 96:1528–1534) and increased sensitivity to numerous inhibitors (Pao and Gallant, 1978, Mol. Gen. Genet. 158:271–277; Stephens et al., 1975, Proc. Natl. Acad. Sci. USA 72:4389–4393).

Two plate growth tests, both based on positive regulatory effects of ppGpp accumulation on amino acid biosynthesis, have been used to study relA mutants. The first test, involves mutant sensitivity to glucose minimal medium supplemented with serine, methionine, and glycine (SMG) (Donachie, 1968, Nature 219:1077–1079); the other test, known as the AT plate test, involves sensitivity to 3-amino-1,2,4-triazole (AT) which is an inhibitor of histidine biosynthesis (Rudd et al., 1985, J. Bacteriol. 163:534–542).

PSII (ppGpp synthetase II), encoded by the SpoT gene, is the second known enzyme which catalyzes the synthesis of ppGpp. PSII is one of the drug target in the present invention. PSII is not activated by amino acid starvation but is active during exponential growth and during certain conditions of environmental stress e.g., phosphate source starvation (Hernandez and Bremer, 1993, J. Biol. Chem. 268:10851–10862). Levels of ppGpp during exponential growth are determined by PSII activity. Id.

Relatively less is known about the products of the SpoT gene. The *E. coli* PSII enzyme has not been characterized biochemically and attempts to obtain homogenous protein from *E. coli* have been unsuccessful suggesting that the enzyme is functionally or physically unstable (Richter, 1969, In Ribosomes (Chambliss, Gaven, Davis, Davis, Kahan and Nomura eds.) 743–765, Univ. Park Press, Baltimore, Md.). PSII activity has, however, been found in certain Bacillus organisms (Sy and Akers, 1976, Biochemistry 15:4399–4403; Fehr and Richter, 1981, J. Bacteriol. 145:68–73). PSII activity in found in the cytoplasm. ibid. SpoT (ppGpp degradase) is the major enzyme activity causing turnover of ppGpp.

It had been suggested that the SpoT gene encodes a single product which may be a bifunctional enzyme capable of catalyzing both ppGpp synthesis and degradation, or that the SpoT gene could encode a regulation of both degradation or synthesis of ppGpp (Cashel and Rudd, 1987; Metzger et al., 1989, J. Biol. Chem. 264:9122–9125; Hernandez and Bremer, 1991, J. Biol. Chem. 266(9):5991–5999; Xiao et al., 1991, J. Biol. Chem. 266(9):5980–5990). PSII activity is reported to be generated during or shortly after spoT mRNA translation. Regulation of spoT encoded activities appears to be responsible for the growth medium-dependent changes in basal levels of ppGpp. PSII appears to catalyze ppGpp synthesis in a ribosome independent fashion. Although the identity of the PSII enzyme has not been proven, the evidence that spoT is the structural gene for PSII and is not simply asserting a regulatory effect is based on the fact that ppGpp is not detectable in strains with deletions in both relA and spoT (Xiao et al., 1991, J. Biol. Chem. 266(9):5980–5990) and the fact that RelA and SpoT have extensive amino acid sequence homology throughout their length. Metzger et al., 1989 J. Biol. Chem. 264:9122–9125.

Further, analysis of the *E. coli* spoT gene has recently identified distinct but overlapping regions involved in ppGpp synthesis and degradation (Gentry and Cashel, 1996, Molecular Microbiol. 19(6):1373–1384). The region containing the first 203 amino acids of the 702 amino acid SpoT protein was confirmed to have ppGpp degradase activity. An overlapping region containing residues 67–374 conferred PSII activity. Id. In addition, PSII activity of *B. stearothermophilus* appears to reside in a monomeric enzyme whose molecular mass is about the same as that of the *E. coli* SpoT product. Fehr and Richter, 1981 J. Bacteriol. 145:68–73.

The effects of ppGpp are pleiotropic, and metabolism of ppGpp is in fact central to many vital bacterial processes. Cellular functions affected by ppGpp include nucleotide metabolism, amino acid metabolism, heat shock and cold shock proteins, basic DNA binding proteins, transport, carbohydrate metabolism, cell wall synthesis and others (Cashel et al., 1996, *Escherichia coli* and Salmonella Cellular and Molecular Biology, ed. Neidhardt, F. C. ASM Press, Washington, D.C., pp. 1458–1496). ppGpp binds directly to the β-subunit of RNA polymerase (Reddy et al., 1995, Mol. Microbiol. 15:255–265). The ppGpp-RNA polymerase complex has a reduced affinity for rRNA and tRNA promoters, so that ribosomal synthesis is decreased when ppGpp accumulates (Zhang & Bremer, 1995, J. Biol. Chem. 370:11181–11189).

The metabolic cycle of ppGpp, as described below, involves the rapid conversion of the nucleotide pppGpp to ppGpp in vivo by removal of the 5' terminal phosphate by the product of the gppA gene (pppGpp 3'-phosphohydrolase) and possibly by the product of the ppx gene. The term ppGpp is therefore used in this invention to designate collectively either or both of these nucleotides, which are essentially interchangeable in their function as regulatory molecules. ppGpp is degraded by ppGpp degradase which is a specific $Mn^{++}$-requiring 3'-pyrophosphohydrolase encoded by the SpoT gene. The cycle is closed through the action of nucleoside 5'-diphosphate kinase (nkd product) on GDP to give GTP (Metzger et al., 1989 J. Biol. Chem. 264:9122–9125). Degradation of ppGpp by the SpoT protein is reduced during carbon source downshift. Net degradation of ppGpp has been found to occur in numerous bacterial systems (Richter et al., 1979, Eur. J. Biochem. 99:57–64).

Despite extensive sequence similarity, SpoT does not share the ribosomal association that has been attributed to RelA (Gentry & Cashel, 1995, J. Bacteriol. 177:3890–3893). Although physiologically less active, degradation of ppGpp has been reported to occur via less active SpoT independent routes. For example, weak activity has been found in cell extracts (An et al., 1979, J. Bacteriol. 137:1100–1110; Heinemeyer et al., 1978, Eur. J. Biochem. 89:125–131). It is contemplated that such SpoT-independent ppGpp degradase activities are also drug targets of the invention for identifying compounds that cause ppGpp accumulation.

Another model of rRNA synthesis control, known as the ribosome feedback regulation model, assumes a repressor role of free or translating ribosomes, either directly or via their activity, without involving a control of PSII activity and ppGpp synthesis (Jinks-Robertson and Nomura, 1987, in *Escherichia coli* and Salmonella Cellular and Molecular Biology, ed. Neidhart, F. C. (ASM Press, Washington, D.C.) pp. 1358–1385; Cole et al., 1987 J.Mol. Biol. 198:383–392). However, later reports have questioned this result.

Further, it has also been suggested, using ppGpp-less strains without detectable ppGpp synthase activity (ppGpp°) that ppGpp is not required for the growth rate control of rRNA synthesis (Gaal and Gourse, 1990, Proc. Natl. Acad. Sci. USA 87:5533–5537). However, Hernandez and Bremer, 1993, J. Biol. Chem. 25:10851–10862, found that growth rate-dependent adjustments of the total RNA synthesis rate do require ppGpp.

5.2. SCREENING ASSAYS OF THE INVENTION

The methods of the invention are designed to identify compounds that cause ppGpp accumulation in test cells. Generally, the screening assays comprise contacting a test compound with test cells for a time sufficient to allow the test compound to cause ppGpp accumulation, and determining the level of ppGpp or the effect of ppGpp accumulation.

The contacting may be effected in any vehicle and by any means using standard protocols, such as serial dilution, and the use of wells, or disks impregnated with a solution or suspension of a test compound. The amount of time allowed for the test compound to cause ppGpp accumulation in the test cells may be determined empirically, such as by running a time course and monitoring the effect of ppGpp accumulation as a function of time. For example, the test cells may be grown in culture to reach a certain phase or density, and then the test cells are exposed to a test compound; or alternatively, the test cells may be grown continuously in the presence of a test compound.

In one embodiment, the invention provides an assay that is based on a $relA^-$, $spoT^+$ strain of test cells which grows normally in rich medium, but not under certain stress conditions as ppGpp synthesis from PSII will be inadequate for normal growth. Compounds that cause ppGpp accumulation by enhancing PSII activity or inhibiting ppGpp degradase allow "paradoxical growth" of the test cells under the stress condition since the test cell would not normally be able to grow. Such compounds are detected by plating the test cells on specialized growth medium that creates these stress conditions. Stress conditions that may be used include but are not limited to metabolic stress, such as carbon or nitrogen starvation, osmotic shock, and pH changes. Examples of such media, not by way of limitation, include minimal medium containing serine hydroxamate, or minimal medium containing the histidine antimetabolite, 3-amino-1,2,4-triazole (AT). Both of these media induce an amino acid starvation condition. Table I shows expected growth of the assay strain in rich medium or on starvation-inducing medium such as mentioned above, in the presence or absence of a ppGpp degradase inhibitor at an appropriate concentration. Typically the appropriate concentration is identified by testing many concentrations as occur, for example, when the compound is impregnated in a paper disk which is then placed on an agar-based medium.

TABLE I

| Medium | Effect of test compound on ppGpp levels | Growth |
|---|---|---|
| Rich | Increase | (+) |
| Rich | Decrease | (+) |
| Starvation-inducing | No effect | (−) |
| Starvation-inducing | Increase | (+) |
| Starvation-inducing | Decrease | (−) |

Accordingly, the invention provides a method for screening for test compounds that cause ppGpp accumulation in bacteria comprising:

(a) contacting a relA deficient test cell under a stress condition such as those mentioned above with a test compound for a time sufficient to allow the test compound to cause ppGpp accumulation in the test cell; and (b) detecting growth of the test cell under the stress condition, wherein an increase in growth of the test cell contacted with the test compound relative to the growth of the test cell not contacted with the test compound, indicates that the test compound causes ppGpp accumulation in the test cell.

In another embodiment, the invention provides a screening assay that uses a strain of *E. coli* with reduced ppGpp synthetic activity and normal degradase activity ($relA^-$, $spoT^+$), but also carrying a reporter gene, such as lacZ (β-galactosidase). This reporter gene is under the control of a promoter that is either negatively or positively controlled by ppGpp.

In one specific embodiment, the expression of the reporter gene in test cells is placed under the control of a promoter that is negatively regulated by ppGpp. By negative regulation is meant that the promoter is transcriptionally active in the absence of ppGpp, and is transcriptionally inactive in the presence of ppGpp. That is, the reporter gene product is produced only when ppGpp levels are low. Under normal conditions, the test cells produce some ppGpp by the PSII enzyme, but this ppGpp is degraded by the degradase activity, and the overall ppGpp levels are low. When the ppGpp level is low, the reporter gene is expressed. In the presence of a compound which, for example, enhances PSII activity or inhibits ppGpp degradase, ppGpp accumulates and as a result, transcription of the reporter gene is repressed. The lack of expression or downregulation of expression of the reporter gene indicates a rise in ppGpp level in the test cells, and identifies the test compound as a candidate for further studies.

In a preferred embodiment, the reporter gene is under the control of a promoter of a ribosomal RNA-encoding gene that is negatively controlled by ppGpp. The test cells are grown on rich medium. For example, and not by way of limitation, the *E. coli* strain VH2733 may be used. This strain contains a relA deletion. Further, the strain contains a lacZ reporter gene operably linked to the rrnB P1 promoter. The rrnB P1 promoter is one of the promoters of the rRNA genes (rrn) and is negatively controlled by ppGpp. The rrnB P1 promoter is initiated by RNA polymerase. When ppGpp is present, it attaches to the RNA polymerase, modifying its structure and activity. This complex cannot form a proper initiation complex at the rrnB P1 promoter. Thus, transcription of rrnB P1 will be limited in the presence of ppGpp. In this strain, the only source of β-galactosidase (β-Gal) is the rrnB P1-linked lacZ gene. The genotype and construction of the VH2733 strain is described in Hernandez, 1991, J. Biol. Chem. 266(9):5991–5999 and Hernandez and Bremer, 1990, J. Biol. Chem. 265(20):11605–11614, both of which are incorporated by reference in their entirety for all purposes.

In a highly preferred embodiment, the assay uses a strain designated VH2736 as deposited with the American Type Culture Collection (ATCC), 10801 University Blvd., Manassas, Va. 20110, on Feb. 10, 1998, and assigned accession number 202090. This relA mutant also contains the spoT$^+$ wildtype, and also contains the lacZ gene fused to the rrnB P1 promoter but contained in a more robust bacterial strain, MG1655. The relevant genotype of VH2736 is MG1655 (*E. coli* K12 wildtype) Δ relA 251::KAN spoT$^+$ malB::P1-lacZ::KAN. The strain VH2736 was made from MG1655 by introducing the Δ relA 251::KAN (described in Xiao et al., 1991, J. Biol. Chem. 266 (9):5980–5990) and malB:: P1-lacZ::KAN (described in Hernandez and Bremer, 1990, J. Biol.Chem. 265 (20): 11605–11614) genes by techniques well known to those skilled in the art. Both references are incorporated herein in their entirety.

The preferred assay strains accumulate a low level of ppGpp from an equilibrium of the PSII enzyme and ppGpp degradase activities. Under these conditions, the lacZ reporter gene is expressed and the assay strain is effectively lac$^+$. In the presence of a compound which, for example, enhances PSII activity or causes ppGpp degradase inhibition, ppGpp accumulates to high levels and therefore transcription of lacZ is inhibited, and the assay strain becomes effectively lac$^-$.

Activity of the lacZ protein can be detected by any medium that allows differentiation of lac$^-$ from lac$^+$ bacterial growth (e.g., lactose and 2,3,5-triphenyl-2H-tetrazolium chloride [tetrazolium], 5-bromo-4-chloro-3-indolyl-β-D-galactoside [X-gal], MacConkey's, or other any such medium known in the art). The preferred medium is lactose-tetrazolium indicator agar. On this medium, lac$^+$ growth is white and lac$^-$ growth is red. The 2,3,5-triphenyl-2H-tetrazolium chloride present in the medium will be reduced by any cell growth to form an insoluble formizan red dye. However, if the cells can metabolize lactose and reduce the pH in the surrounding medium, formation of the red dye is prevented. In the absence of a desired compound such as one, for example, which is a ppGpp degradase inhibitor, the strain accumulative low levels of ppGpp such that the overall levels are too low to inhibit lacZ expression. Therefore, LacZ gene product is produced and bacterial growth is white. In the presence of a compound that inhibits ppGpp degradase, ppGpp accumulates to high levels, the lacZ gene is and bacterial growth is red. Eventually, if ppGpp levels are driven high enough, they will become toxic and limit growth. Therefore, desired compounds will also cause a zone of growth inhibition around the point of application. In the ideal case, desired compounds will cause a zone of growth inhibition with red growth at the periphery. Past this periphery cells should grow normally and be white. Table 2 shows expected results when the assay strain is grown in lactose-tetrazolium medium, in the presence or absence of a compound which causes ppGpp accumulation.

TABLE II

| Effect of test compound on ppGpp levels | ppGpp levels | lacZ transcription | Color of growth |
|---|---|---|---|
| No effect | Baseline | (+) | White |
| Increase | High | (−) | Red |
| Decrease | Low | (+) | White |

Accordingly, the invention provides a method for screening for test compounds that cause ppGpp accumulation in bacteria comprising:

(a) contacting a relA deficient test cell with a test compound for a time sufficient to allow the test compound to cause ppGpp accumulation in the test cell, wherein the test cell contains a reporter gene operably linked to a promoter which is negatively regulated by ppGpp, and (b) detecting the expression of the reporter gene in the test cell, wherein a decrease in the expression of the reporter gene in the test cell contacted with the test compound relative to the expression of the reporter gene in a test cell not contacted with the test compound, indicates that the test compound causes ppGpp accumulation in the test cell.

In another specific embodiment, the expression of the reporter gene in test cells is placed under the control of a promoter that is positively regulated by ppGpp. By positive regulation is meant that the promoter requires ppGpp for full transcriptional activity. That is, the reporter gene product is produced only when ppGpp levels are high. In the test cells, transcription of the reporter gene is up-regulated when ppGpp levels are high.

In a preferred embodiment, the assay uses a strain of *E. coli* with reduced PSI activity and normal degradase activity as described above (relA$^-$, spoT$^+$), with the reporter gene under the control of a promoter that is positively controlled by ppGpp. For example, and not by way of limitation, the reporter gene, such as but not limited to the β-galactosidase (lacZ) gene, may be placed under the control of a promoter from a gene encoding a protein involved in histidine biosynthesis, such as hisP$_1$, hisP$_2$. Previous studies indicated that spoT mutants with defective ppGpp degradation activity show overexpression of the his operon due to elevated ppGpp levels (Rudd et al., 1985, J. Bacteriol. 163:534–542 (in *Salmonella typhimurium*); and Sarubbi et al., 1988, Mol. Gen. Genet. 213:214–222 (in *Escherichia coli*).)

The test cells are plated on rich medium on which the test cells grow and produce some ppGpp by the PSII enzyme. But this ppGpp is degraded by the degradase activity and the overall ppGpp levels are low. Under these conditions, there is only a low background level of reporter gene expression from the positively regulated promoter, since ppGpp is required for full expression. In the presence of a compound which causes the accumulation of ppGpp to high levels, such as, for example, a ppGpp degradase inhibitor, ppGpp accumulates and therefore the reporter gene is fully expressed.

Activity of the reporter gene product, such as β-galactosidase, can be detected by any medium that allows differentiation of lac⁻ from lac⁺ bacterial growth (e.g., lactose-tetrazolium, 5-bromo-4-chloro-3-indolyl-β-D-galactoside [X-gal], MacConkey's, or the like). The preferred medium contains X-gal. On this medium, β-galactosidase activity results in a blue color. In the absence of such a ppGpp degradase inhibitor, negligible β-galactosidase is produced and the bacterial growth is only slightly blue. In the presence of a compound that inhibits ppGpp degradase, ppGpp accumulates and allows maximum β-galactosidase production giving the bacterial growth a pronounced blue color which is easily distinguishable from the much lighter blue background. Again, desired compounds will cause a zone of growth inhibition with a dark blue ring at the periphery. Table 3 shows the expected results when the test cells are grown in a X-gal-containing medium, in the presence or absence of a compound which causes ppGpp accumulation.

TABLE III

| Effect of test compound on ppGpp levels | ppGpp levels | lacZ transcription | Color of growth |
| --- | --- | --- | --- |
| No effect | Baseline | Baseline | White |
| Increase | High | (+) | Blue |
| Decrease | Low | (−) | White |

Accordingly, the invention provides a method for screening for test compounds that cause ppGpp accumulation in bacteria comprising:
(a) contacting a relA deficient test cell with a test compound for a time sufficient to allow the test compound to cause ppGpp accumulation in the test cell, wherein the test cell contains a reporter gene operably linked to a promoter which is positively regulated by ppGpp, and
(b) detecting the expression of the reporter gene in the test cell, wherein an increase in the expression of the reporter in the test cell contacted with the test compound relative to the expression of the reporter gene in a test cell not contacted with the test compound, indicates that the test compound causes ppGpp accumulation in the test cell.

It should be noted that, since in vitro and in vivo conditions provide different environments, certain compounds which give a certain result in vitro result will not necessarily give the same result in vivo. For example, two compounds that have been reported to inhibit ppGpp degradase in vitro did not test positive in the assay of the invention: tetracycline and picolinic acid. Both have been reported to indirectly inhibit by chelation of manganese (manganese is required for ppGpp degradase activity).

In the case of tetracycline, inhibition was reported in an in vitro reaction when the antibiotic was added to a final concentration of about 400 μg/ml (Richter, 1980, Arch. Microbiol. 124:229–232). This concentration would be impossible to achieve in whole cells since concentrations above 50 μg/ml completely inhibit bacterial growth. Thus, the lack of a red ring is explained by the discrepancy between the concentration needed for degradase inhibition and the concentration that can be tolerated by growing bacteria.

Picolinic acid is a hydrophobic compound which is only sparingly soluble in water, so diffusion through the solid agar and away from the point of applicatin is inefficient. In fact, picolinate did not cause a zone of inhibition in the agar assay although it inhibited growth in liquid cultures.

5.3. TEST CELLS OF THE INVENTION

The test cells of the invention are employed in screening assays for the identification of compounds that cause ppGpp accumulation.

In one embodiment, the invention uses a strain of test bacterial cells that is deficient at the relA locus or its equivalent. Such strains (also referred to as "relaxed" strains) are known in the art. These cells lack PSI activity which synthesizes ppGpp in quantities sufficient to inhibit ribosomal RNA synthesis under certain physiological conditions. The relA locus or its equivalent in these cells may either be deleted or mutated to the extent that the gene product is no longer functional. To make a relA⁻ bacterial strain, the relA gene or its equivalent in wildtype bacteria may be mutagenized or deleted by genetic methods or recombinant DNA techniques well known in the art. These cells may also be spoT⁺ which provides normal PSII activity and normal ppGpp degradase activity.

In another embodiment, the invention uses a strain of test bacterial cells that is deficient in relA or its equivalent, and that comprises a genetic sequence encoding a reporter molecule, wherein the expression of said genetic sequence is regulated by positively or negatively by ppGpp.

In a more specific embodiment, the relA⁻ test cells comprise a reporter construct comprising a genetic sequence encoding a reporter molecule (i.e., a reporter gene sequence), said genetic sequence is operably linked to a ppGpp-responsive promoter, i.e., a promoter which is regulated positively or negatively by the level of ppGpp in the test cells.

In various embodiments, the reporter gene sequence of the invention can include any genetic sequence, preferably DNA sequence which encodes a detectable gene product (i.e., a peptide or polypeptide). The genetic sequences encoding detectable reporter gene products are well known to those of skill in the art. The reporter gene sequence does not encode necessarily a detectable peptide or polypeptide, since the messenger RNAs of the reporter gene sequence can be detected and quantified.

Any relA⁻ bacterial cells that can express a reporter gene under the control of a ppGpp-responsive promoter may be used. Test bacterial cells may be obtained from private laboratory deposits, public culture collections such as the American Type Culture Collection, or from commercial suppliers. It is desirable to use bacteria which have been developed for drug screening processes, and that conditions for their growth, maintenance, and manipulations are known.

The most preferred bacterial species that is useful as test cells is *Escherichia coli*. Other preferred bacterial species may include but not limited to *Bacillus subtilis*, and *Pseudomonas aeuroginosa*. For example, and not by way of limitation, a highly preferred strain of test cells is *E. Coli* strain VH2736, as deposited with the American Type Culture Collection (ATCC), 10801 University Blvd., Manassas, Va. 20110, on Feb. 10, 1998.

*Escherichia coli* can be used as a model of many bacteria. Test compounds that specifically inhibit host transcription of *E. coli* test cells are expected to have a similar inhibitory effect on the transcription of pathogenic species, such as but not limited to, Vibrio species, Pseudomonas species, Acinetobacter species, Bordetella species, Campylobacter species, Haemophilus species, Neisseria species and Enterobacteriaceae species, such as Salmonella, Enterobater, Klebsiella, Yersinia, Proteus, Serratia, and Staphylococcus species, Streptococcus species, Corynebacterium species, Listeria species and Bacillus species. It is also expected that positive test compounds will be effective as an antibiotic against multidrug-resistant strains of these pathogenic species, such as β-lactam-resistant strains of E. coli.

Standard molecular biology techniques can be used to construct reporter gene constructs containing the ppGpp-responsive promoter and translational control signals if necessary, reporter gene sequence, and other regulatory sequence, such as terminators.

In the present invention, the reporter gene sequence(s) ray be inserted into a recombinant expression vector. The term "reporter gene constructs" refers to a plasmid, virus or other vehicle known in the art that has been manipulated by insertion or incorporation of reporter gene sequences. Such reporter gene constructs of the invention are preferably plasmids which contain a ppGpp-responsive promoter sequence which is operably associated with the inserted reporter gene sequence. It typically contains an origin of replication as well as specific genes which allow phenotypic selection of the transformed cells.

"Operably-associated" or "operably-linked" refers to an association in which the heterologous promoter and the reporter gene sequence are joined and positioned in such a way as to permit transcription. Two or more sequences, such as a promoter and any other nucleic acid sequences are operably-associated if transcription commencing in the heterologous promoter will produce an RNA transcript of the operably-associated sequences.

A reporter gene construct useful in the invention may also contain selectable or screenable marker genes for initially isolating, identifying or tracking test cells that contain heterologous DNA. The reporter gene construct may also provide unique or conveniently located restriction sites to allow severing and/or rearranging portions of the DNA inserts in a reporter gene construct. More than one reporter genes may be inserted into the construct such that the test cells containing the resulting construct can be assayed by different means.

Introduction of the reporter gene construct into bacterial cells DNA may be carried out by conventional techniques well known to those skilled in the art, such as transformation, conjugation, and transduction. For example, where the host is E. coli, competent cells which are capable of DNA uptake can be prepared from cells harvested after exponential growth and subsequently treated by the $CaCl_2$ method using procedures well known in the art. Alternatively, $MgCl_2$ or RbCl could be used.

In addition to conventional chemical methods of transformation, the plasmid vectors of the invention may be introduced into a host cell by physical means, such as by electroporation or microinjection. Electroporation allows transfer of the vector by high voltage electric impulse, which creates pores in the plasma membrane of the host and is performed according to methods well known in the art. Additionally, cloned DNA can be introduced into host cells by protoplast fusion, using methods well known in the art.

The host cells which contain the reporter gene sequence and which express the reporter gene product may be identified by at least four general approaches; (a) DNA-DNA or DNA-RNA hybridization; (b) the presence or absence of "marker" gene functions (e.g., resistance to antibiotics); (c) assessing the level of transcription as measured by the expression of reporter mRNA transcripts in the host cell; and (d) detection of the reporter gene product as measured by immunoassay or by its biological activity.

The test cells may be cultured under standard conditions of temperature, incubation time, optical density, plating density and media composition corresponding to the nutritional and physiological requirements of the bacteria. However, conditions for maintenance and growth of the test cell may be different from those for assaying candidate test compounds in the screening methods of the invention. Modified culture conditions and media are used to facilitate detection of the expression of a reporter molecule. Any techniques known in the art may be applied to establish the optimal conditions.

Test cell strains, cell cultures, cell lines generated by the above-described methods for the screening assays may be expanded, stored and retrieved by any techniques known in the art that is appropriate to the test cell. For example, the test cells of the invention can be preserved by stab culture, plate culture, or in glycerol suspensions and cryopreserved in a freezer (at $-20°$ C. to $-100°$ C.) or under liquid nitrogen ($-176°$ C. to $-196°$ C.).

The term "reporter gene" as used herein refers to any genetic sequence that is detectable and distinguishable from other genetic sequences present in test cells. Preferably, the reporter gene sequence encodes a protein that is readily detectable either by its presence, or by its activity that results in the generation of a detectable signal. A reporter gene is used in the invention to monitor and report the activity of a ppGpp-responsive promoter in test cells.

A reporter gene encodes a reporter molecule which is capable of directly or indirectly generating a detectable signal. Generally, although not necessarily, the reporter gene encodes RNA and detectable protein that are not otherwise produced by the test cells. Many reporter genes have been described, and some are commercially available for the study of gene regulation. See, for example, Alam and Cook, 1990, Anal. Biochem. 188:245–254, the disclosure of which is incorporated herein by reference.

Any antigenic peptide or protein that can be detected by an antibody can be used as a reporter, for example, growth hormone (Selden et al., Mol. Cell Biol., 6:3173). To facilitate detection by antibody binding in immunoassays, antigenic reporter molecules that are secreted or attached on the test cell surface are preferred.

For convenience and efficiency, enzymatic reporters and light-emitting reporters are preferred for the screening assays of the invention. Accordingly, the invention encompasses histochemical, colorimetric and fluorometric assays.

A variety of enzymes may be used as a reporter which includes but are not limited to β-galactosidase (Nolan et al. 1988, Proc. Natl. Acad. Sci. USA 85:2603–2607), chloramphenicol acetyltransferase (CAT; Gorman et al., 1982, Mol Cell Biol, 2:1044; Prost et al., 1986, Gene 45:107–111), β-lactamase, β-glucuronidase and alkaline phosphatase (Berger et al., 1988, Gene 66:1–10; Cullen et al., 1992, Methods Enzymol; 216:362–368). Transcription of the reporter gene leads to production of the enzyme in test cells. The amount of enzyme present can be measured via its enzymatic action on a substrate resulting in the formation of a detectable reaction product. The methods of the invention provides means for determining the amount of reaction product, wherein the amount of reaction product generated or the remaining amount of substrate is related to the amount of enzyme activity. For some enzymes, such as β-galactosidase, β-glucuronidase and β-lactamase, fluorogenic substrates are available that allow the enzyme to covert such substrates into detectable fluorescent products (see, for example, U.S. Pat. No. 5,070,012, and WO 96/30540).

The most preferred reporter gene of the invention is the LacZ gene encoding *E. coli* β-galactosidase. The enzyme is very stable and has a broad specificity so as to allow the use of different chromogenic or fluorogenic substrates, such as but not limited to lactose 2,3,5-triphenyl-2H-tetrazolium (lactose-tetrazolium), 5-bromo-4-chloro-3-indolyl-β-D-galactoside (X-gal), and fluorescein galactopyranoside (Molecular Probes, Orgeon). See, Nolan et al. 1988, Proc. Natl. Acad. Sci. USA 85:2603–2607.

Another commonly used reporter gene is the *E. Coli* β-glucuronidase gene (GUS; Gallagher, 1992, in "GUS protocols", Academic Press) which can be used with various histochemical and fluorogenic substrates, such as X-glucuronide, and 4-methylumbelliferyl glucuronide.

A variety of bioluminescent, chemiluminescent and fluorescent proteins can also be used as light-emitting reporters in the invention. One type of such reporters, which are enzymes and require cofactor(s) to emit light, include but are not limited to, the bacterial luciferase (luxAB gene product) of *Vibrio harveyi* (Karp, 1989, Biochim. Biophys. Acta 1007:84–90; Stewart et al. 1992, J Gen Microbiol, 138:1289–1300), and the luciferase from firefly, *Photinus pyralis* (De Wet et al. 1987, Mol. Cell. Biol. 7:725–737).

Another type of light-emitting reporter, which does not require substrates or cofactors, includes but are not limited to the wild type green fluorescent protein (GFP) of *Victoria aequoria* (Chalfie et al. 1994, Science 263:802–805), and modified GFPs (Heim et al. 1995, Nature 373:663–4; PCT publication WO 96/23810). Transcription and translation of this type of reporter gene leads to the accumulation of the fluorescent protein in test cells, which can be measured by a device, such as a fluorimeter, or a flow cytometer. Methods for performing assays on fluorescent materials are well known in the art and are described in, e.g., Lackowicz, J. R., 1983, Principles of Fluorescence Spectroscopy, New York:Plenum Press.

Depending on the screening technique and nature of the signal used to assay the reporter gene expression, a reporter regimen can be used to aid directly or indirectly the generation of a detectable signal by a reporter molecule. A reporter regimen comprises compositions that enable and support signal generation by the reporter, such as substrates and cofactors for reporter molecules that are enzymes; e.g., lactose-tetrazolium medium. Such compositions are well known in the art. Components of a reporter regimen may be supplied to the test cells during any step of the screening assay.

5.4. SPECIFIC EMBODIMENTS

The invention may be better understood by the following description of illustrative embodiments which are not intended to be limiting.

5.4.1. DETERMINATION OF PARADOXICAL GROWTH

This embodiment uses an *E. coli* strain such as, and not by way of limitation, VH2733 or VH2736, with normal PSII activity and normal degradase activity (spoT+), but lacking PSI activity due to a mutation or deletion at the relA locus.

The assay strain is plated as a lawn on solid medium containing AT, for example, at a concentration of 15 mM. Test compounds are then applied to the medium in wells or on disks. Paradoxical growth is determined by visually comparing growth around the well or disk containing the test compound to growth in control areas which are free of the test compound. Comparison of test and control areas is done at the same time point. Compounds that cause ppGpp accumulation show a ring of enhanced growth at the periphery. Compounds which cause ppGpp accumulation, such as NaN$_3$ (sodium azide) (Murray and Bremer, 1996, J. Mol. Biol. 259:41–57), or 1,10-phenanthroline are included in the assay as a control since the test strain is not expected to grow on the medium in the absence of a ppGpp degradase inhibitor.

That is, paradoxical growth is seen around the points of application, and this growth diminishes as NaN$_3$ concentration decreases.

5.4.2. DETERMINATION OF ppGpp ACCUMULATION USING A REPORTER GENE NEGATIVELY CONTROLLED BY ppGpp

In this embodiment, the assay strain is an *E. coli* strain which is a relA mutant with reduced PSI synthetase activity but with normal or wildtype PSII synthetase activity and degradase activity (spoT+). This strain also contains the reporter gene lacZ under the control of a promoter which is negatively controlled by ppGpp. The strain is plated as a is lawn on solid lactose tetrazolium medium (50 μ/ml 2,3,5-triphenyl-2H tetrazolium chloride), and compounds are added in wells, as described in Section 5.4.1. The cells added to the agar plate are actively growing (log phase) but dilute enough to avoid crowding of cells and inaccurate results. Colony color around the well or disk containing test compound is compared to control areas of the plate that are free of test compound. Comparison of test and control areas is done at the same time point. Compounds that cause ppGpp accumulation are expected to show a ring of red growth around the well or disk. In other lactose differential medium, results will be analogous but the positive and negative readout will depend on the indicator of lactose fermentation. Compounds that cause ppGpp accumulation, such as NaN$_3$, 1,10-phenanthroline or picolinic acid is included in the assay as a positive control. At high concentrations NaN$_3$ (sodium azide) is toxic, and therefore there is a zone of inhibited bacterial growth close to the disk. At some distance from the disk, a ring of red growth is seen, indicating that at some lower concentration NaN$_3$ is allowing ppGpp accumulation and the cells have become lac−.

Accordingly, the invention provides a method for screening for test compounds that cause ppGpp accumulation in bacteria comprising:

(a) culturing a strain of relA deficient test cell which contains a β-galactosidase gene operably linked to a promoter that is negatively regulated by ppGpp, such as *E. coli* strain VH2736;

(b) inoculating a plate containing a medium comprising lactose and 2,3,5-triphenyl-2H-tetrazolium with the test cells;

(c) adding a test compound to a point of application, such as a well, in the plate and incubating the plate for a time sufficient to allow the test compound to contact the test cell and cause ppGpp accumulation;

(d) detecting a red coloration and growth of the test cells contacted with the test compound, wherein the red coloration indicates a lack of expression of the β-galactosidase gene in the test cells; and (e) comparing the coloration and growth of test cells not contacted with the test compound;

wherein an increase in red coloration and growth of the test cell contacting the test compound relative to the coloration and growth of test cells not contacting the test compound indicates that the test compound causes ppGpp accumulation in the test cell.

5.4.3. DETERMINATION OF ppGpp ACCUMULATION USING A REPORTER GENE POSITIVELY CONTROLLED BY ppGpp

In this embodiment, the assay strain is a relA deficient mutant with reduced PSI synthetase activity but with normal PSII synthetase activity and normal degradase activity with a lacZ reporter gene under the control of a promoter which is positively controlled by ppGpp. This strain is plated as a lawn on solid medium, and test compounds are added in wells, as described in Section 5.4.1. The medium can be LB (as described in Maniatis et al., MOLECULAR CLONING A Laboratory Manual, Cold Spring Harbor Press, eds. 1982) or similar rich medium containing X-gal (80 µg/ml) as a chromogenic substrate for the β-galactosidase enzyme. Colony color around the well or disk containing test compound is compared to control areas of the plate that are free of test compound. Comparison of test and control areas is done at the same time point. Compounds that cause ppGpp accumulation are expected to show a ring of blue growth around the well or disk. In other lactose differential medium, results will be analogous but the positive and negative readout will depend on the indicator of lactose fermentation. A known inhibitor of ppGpp degradase, such as $NaN_3$, 1,10-phenanthroline or picolinic acid is included in every plate as a positive control. At high concentrations this compound is toxic, and therefore there is a zone of inhibited bacterial growth close to the disk. At some distance from the disk, a ring of blue growth is seen, indicating that at some lower concentration, $NaN_3$ is allowing ppGpp accumulation and the cells have become $lac^+$.

Accordingly, the invention provides a method for screening for test compounds that cause ppGpp accumulation in bacteria comprising:

(a) culturing a relA deficient strain of *E. coli* test cell wherein the test cells contains a β-galactosidase gene operably linked to a promoter which is positively regulated by ppGpp;

(b) inoculating a plate containing a medium comprising 5-bromo-4-chloro-3-indolyl-β-D-galactoside with the test cells;

(c) adding a test compound to a point of application, such as a well, in the plate and incubating the plate for a time sufficient to allow the test compound to contact the test cell and cause ppGpp accumulation;

(d) detecting a blue coloration and an inhibition of growth of the test cells contacted with the test compound, wherein the blue coloration indicates expression of the β-galactosidase gene in the test cells; and (e) comparing the coloration and growth of test cells not contacted with the test compound;

wherein an increase in blue coloration, and an inhibition of growth of the test cell contacting the test compound relative to the coloration and growth of test cells not contacting the test compound indicates that the test compound causes ppGpp accumulation in the test cell.

5.5. ELIMINATION OF β-GALACTOSIDASE INHIBITORS

Compounds that inhibit β-galactosidase enzymatic activity will give false positive results in the primary assay of Section 5.4.2. Such compounds can be eliminated by testing against a standard preparation of β-galactosidase protein using a commercial kit with a chemiluminescent substrate (Tropix), or by repeating the primary assay using a strain of bacteria that expresses lacZ from a promoter that is not responsive to ppGpp. Compounds that inhibit β-galactosidase are considered false positive and are not carried forward. All compounds which do not inhibit β-galactosidase are potential inhibitors of ppGpp degradase and are carried through to the secondary assays described below.

Alternatively, after screening by using the methods described in the primary assay in Section 5.4.2., elimination of false positive results may be carried out by using a second screening such as, for example, the methods described in Section 5.4.3.

5.6. TLC ANALYSIS OF ppGpp

Intracellular levels of ppGpp can be accurately detected and quantitated by labeling cells in vivo with $^{32}P$ orthophosphate, which is incorporated into all phosphorylated cellular components including ATP, GTP, pppGpp and ppGpp. The labeled nucleotide products are extracted using formic acid, then separated (TLC) by thin layer chromatography. The addition of putative ppGpp degradase inhibitors to cultures of cells being labeled should lead to an increase in intracellular ppGpp. Thus, a TLC assay will establish promising compounds as true modulators of intracellular ppGpp levels.

Methods for TLC known in the art may be used such as the TLC assay (M. Cashel, 1994, Methods in Molecular Genetics, vol. 3, Molecular Microbiology Techniques, Part A, ed. Adolph, K. W. (Academic Press, New York) pp. 341–356) which is incorporated by reference in its entirety. Accumulation of ppGpp over basal levels is detected in cells grown in liquid media with defined phosphate concentrations (approximately 0.4 mM) low enough to achieve $^{32}P$ specific activities enabling nucleotide detection. Other methods of labeling well known in the art are also applicable. Cells are uniformly labeled by growth in the presence of radioactive orthophosphate (200–250 µCi/mM) for two generations prior to the addition of test compound. Labeled nucleotides are extracted by adding concentrated formic acid and freeze-thawing the cell suspension. Labeled nucleotides are resolved by TLC, using polyethyleneimine cellulose (PEI) plates in a concentrated phosphate buffer solvent. This solvent lowers background by continuously eluting excessive radioactive phosphate present in extracts. The separated nucleotide species are visualized by autoradiography. Quantitation can be done by cutting out radioactive spots and counting them in a liquid scintillation counter, or by densitometry or other methods known to those skilled in the art. A diluted aliquot of an unchromatographed sample can be used as a baseline for calculating the phosphate specific activity achieved in the cell and, in turn, the relative abundance of ppGpp, ppGpp and GTP.

5.7. DETERMINATION OF ENZYMATIC ACTIVITY USING PARTIALLY PURIFIED ppGpp DEGRADASE

Active ppGpp degradase (SpoT protein) can be isolated from *E. coli* and used in an in vitro enzyme assay in order to assess the effects of compounds on the partially purified enzyme.

5.7.1. PREPARATION OF RADIOLABELED SUBSTRATE

Ribosomes with active ppGpp synthetase I (relA) are prepared from a strain of *E. coli* that carries a plasmid encoding the relA gene under the control of an inducible promoter. These ribosomes are then combined with GTP and ATP, and the relA protein synthesizes both ppGpp and pppGpp. CF3120 cells are grown in Luria broth containing 100 µg/ml ampicillin to an $A_{600}$ of 1.5. relA expression is then induced by the addition of IPTG to a final concentration of 1 mM. Cells are incubated for 1 hour, then harvested by centrifugation. The cell pellet is washed in ribosomal buffer (50 mM Tris acetate [pH 8.0], 15 mM Mg acetate, 60 mM potassium acetate, 27 mM ammonium acetate, 1 mM DTT and 0.2 mM EDTA) and the resulting cell pellet is stored at −70° C. The frozen cell pellet is resuspended in 2 volumes (w/v) of ribosomal buffer then cells are lysed by French press. The lysate is centrifuged at 11,000×g for 40 min at 4° C. The supernatant is centrifuged at 30,000 rpm in a Beckman Ti65 (or equivalent) for 4 hrs at 4° C. The resulting pellet of ribosomes and membranes is combined with 2.5 volumes of cold ribosomal buffer, transferred to a beaker and stirred slowly overnight at 4° C. The solution is then centrifuged at 7,500×g for 15 min at 4° C. to remove undissolved debris. The supernatant is removed and ribosomal buffer is added to bring the suspension to 4× (w/v) with respect to the original weight of the cells. A 5 ml cushion of 40% sucrose in ribosomal buffer is placed in a 30 ml ultracentrifuge tube then the ribosomal suspension is carefully layered on top, filling the tube. The preparation is centrifuged at 32,000 rpm in a Beckman Ti65 (or equivalent) for 4 hrs at 4° C. The supernatant is discarded and the pellet is transferred to a beaker containing a minimal volume of cold ribosomal buffer. The mixture is stirred at 4° C. until resuspended then stored by dropping drops into a beaker filled with liquid nitrogen. The drops freeze and can be stored in vials at −70° C. Just before use, drops are transferred to a tube and thawed on ice.

The ribosomes are used to synthesize radiolabeled ppGpp and pppGpp as follows. A reaction mixture containing 0.5 mM GTP (mixed with $^{32}$P alpha GTP), 2 mM ATP and ribosome preparation is incubated overnight at room temperature. The reaction is stopped by adding phenol-chloroform, and diluted to 5 ml with 20 mM Tris-Cl (pH 6.8), 6 M urea, 0.1 mM EDTA and 40 mM LiCl. Both ppGpp and pppGpp are produced in the reaction.

To separate the reaction components (ppGpp, pppGpp, GTP and ATP), the reaction mixture is loaded to a 0.9×40 cm QAE-Sephadex column equilibrated in the same buffer. The column is washed in the same buffer, then the reaction products are eluted with a linear gradient of LiCl from 0.1 mM to 0.5 mM. The separation of ppGpp, pppGpp, GTP and ATP is assessed by TLC and autoradiography, then separate pools are made of fractions containing ppGpp or pppGpp. Either of these products can be used in the degradase reaction described below. The pooled fractions are diluted 10–20 fold in 20 mM Tris-Cl (pH 6.8), 0.1 mM EDTA and 40 mM LiCl, then applied to a 1 ml QAE-Sephadex column equilibrated in the same buffer. The ppGpp or pppGpp is eluted with 4 M LiCl, then precipitated by adding 5 volumes of ethanol (at −20° C.). The mixture is centrifuged and the pellet is resuspended in TE and stored at −20° C.

5.7.2. PREPARATION OF ACTIVE ppGpp DEGRADASE

Active ppGpp degradase is prepared from a strain of *E. coli* that overexpresses spoT. In a preferred embodiment, overexpression of spoT is accomplished by induction of an IPTG-responsive promoter in a plasmid carrying the gene for spoT. Cells are grown at 30° C. in Luria broth supplemented with 0.2% glucose, 40 mM potassium phosphate (pH 7.5) and appropriate antibiotics. When the culture reaches an A600 of 1.0, expression of spoT is induced by the addition of IPTG to a final concentration of 1 mM. Cells are incubated for an additional 2 hrs, then harvested by centrifugation, washed in lysis buffer (50 mM Tris acetate, [pH 8.0], 5 mM EDTA, 0.23 M NaCl, 100 µ/ml PMSF, 1 mM DTT), then stored at −80° C. The frozen cell pellet is resuspended in 3 volumes of lysis buffer and cells are lysed using a French press. The resulting cell lysate is centrifuged at 11,000×g. SpoT protein is found in both the supernatant and the pellet. SpoT protein is extracted from the pellet by adding 50 ml TGED buffer containing lM NaCl and stirring at 4° C. for 1 hr (TGED buffer=10 mM Tris, [pH 8.0], 5% glycerol, 0.1 mM EDTA, 0.1, 0.1 mM DTT). Ammonium sulfate is added to the extracted pellet solution and to the supernatant, to a final volume of 25%. The mixture is stirred at 4° C. for 1 hr, then precipitated proteins (including SpoT) are recovered by centrifugation at 11,000×g. The pellet is dissolved in 7 ml of TGED buffer containing 1M NaCl and 50% glycerol, then applied to a 200 ml gel filtration column (for example, Sephacryl 200) equilibrated with TGED containing 1M NaCl. Fractions containing SpoT protein are pooled and dialyzed against SpoT storage buffer (TGED buffer containing 1M NaCl and 10% glycerol). The resulting SpoT preparation is stored at −70° C. The preparation contains partially purified active SpoT protein and can be used for enzyme assays. If further purification is desired, the preparation is applied to a 5 ml heparin column (for example, BioRad) that has been equilibrated with 300 mM NaCl, 5% glycerol. SpoT protein is eluted with a 100 ml continuous gradient of 300 mM to 1M NaCl, 5% glycerol. Fractions containing SpoT are pooled and stored at −70° C. in SpoT storage buffer.

5.7.3. DEGRADASE ASSAY

Purified SpoT protein is combined with radiolabeled pppGpp (or ppGpp) 10× reaction buffer (500 mM Tris-Cl (pH 8.0), 1M Mg acetate, 10 mM DTT) and $MnCl_2$ to a final concentration of 1 mM. The reactions are incubated, with and without added test compound, at room temperature. Aliquots are removed at various time points up to 20 minutes (for example, 0.5, 1, 2, 5, 10 and 20 min) and spotted to PEI TLC plates. The reaction substrate and products are separated by developing the TLC plate in phosphate buffer and visualized by autoradiography. The amount of product (GTP and pyrophosphate) can be quantitated by liquid scintillation counting or other methods known in the art. Degradase activity can be compared in the presence and absence of test compound, thus verifying the effects of bona fide inhibitors of degradase enzymatic activity.

5.8. DETERMINATION OF MIC

The minimum inhibitory concentration (MIC) against bacterial organisms is determined for each compound that is positive in both the primary assay (using lactose tetrazolium as described in Section 5.4.2) and secondary assay (using X-gal as described in Section 5.4.3). Methods known in the art may be used such as broth microdilution testing, using a range of concentrations of each test compound (1993, National Committee for Clinical Laboratory Standards). Methods for Dilution Antimicrobial Susceptibility Tests For Bacteria That Grow Aerobically—Third Edition: Approved Standard, M7-A3). The MIC against a variety of pathogens are determined using the same method. Pathogenic species to be tested generally include: *E. coli, Enterococcus faecium, Enterococcus faecalis, Streptococcus pneumoniae,*

*Staphylococcus aureus, Klebsiella pneumoniae, Pseudomonas aeruginosa, Staphylococcus epidermis, Shigella flexneri,* and *Salmonella typhimurium.*

5.9. CYTOTOXICITY TESTING

Unfortunately, toxicity does not always arise from the same mechanism of action as is responsible for growth inhibition in the targeted microorganism. Therefore, the selectivity of the target should not be assessed solely on the basis of these results.

Cytotoxity can be measured by methods known in the art. One such method is assessing growth of mammalian cells in the presence of the test compound, using a protein binding dye, sulforhodamine B (SRB). SRB binds electrostatically to basic amino acids. Binding and solubilization of the dye can be controlled by changes in pH. SRB binds stoichiometrically to proteins in one pH range but can be solubilized and extracted for measurement in another. An increase in total protein is correlated to cell growth. Cell growth in the presence of compound is compared to growth without added compound to establish a growth inhibitory concentration ($GI_{50}$) (Skehan et al., 1990, J. Natl. Cancer. Inst., 82:1107–1112). Another method of measuring cytoxicity which may be used in an assay containing 3[4,5-dimethylthiazol-2-yl]-2,5,-diphenyltetrazolium bromide/2, 3-bis[2-methoxy-4-nitro-5-sulfophenyl]-2H-tetrazolium-5-carboxanilide inner salt ("MTT/XTT") as described in Mosmann T., 1983, J. Immunol. Methods, 65:55–63, which is incorporated by reference in its entirety for all purposes.

5.10. ANTIBIOTIC AGENTS IDENTIFIED BY METHODS OF THE INVENTION

In yet another embodiment, the invention provides novel antibiotic agents discovered by the methods described above. These antibiotic agents are capable of causing ppGpp accumulation in a bacterial cell, leading to downregulation of rRNA synthesis, and ultimately to a reduction or inhibition of bacterial growth. These agents may, for example, act by enhancing PSII activity, and/or inhibiting ppGpp degradase activity, and are expected to be effective in a variety of species of bacteria, including infectious pathogenic bacteria. The invention also includes novel pharmaceutical compositions which comprise antibiotic agents discovered as described above formulated in pharmaceutically acceptable formulations.

In another embodiment, the invention features a method for treating a subject infected with an infectious agent by administering to that subject a therapeutically effective amount of an antibiotic agent which causes ppGpp accumulation (for example, by enhancing PSII activity, and/or inhibiting ppGpp degradase activity) in the infectious agent as determined by the assays of the invention. Such administration can be by any method known to those skilled in the art, for example, by topical application or by systemic administration.

In yet another embodiment, antibiotic agents of the present invention can be used to treat contaminated items, such as crops, wood, metal or plastic and the like, by methods such as, but not limited to, spraying or dusting of that agent onto the contaminated item, or impregnating that agent into the item.

By "therapeutically effective amount" is meant an amount that relieves (to some extent) one or more symptoms of the disease or condition in the patient. Additionally, by "therapeutically effective amount" is meant an amount that returns to normal, either partially or completely, physiological or biochemical parameters associated with or causative of a bacterial disease or condition.

5.10.1. FORMULATION

The antibiotic compounds identified by methods of the invention may be formulated into pharmaceutical preparations for administration to animals for treatment of a variety of infectious diseases. Compositions comprising a compound of the invention formulated in a compatible pharmaceutical carrier may be prepared, packaged, labelled for treatment of and used for the treatment of the indicated infectious diseases caused by microorganisms, such as those listed infra in Section 5.9.3.

If the antibiotic compound is water-soluble, then it may be formulated in an appropriate buffer, for example, phosphate buffered saline or other physiologically compatible solutions. Alternatively, if the resulting complex has poor solubility in aqueous solvents, then it may be formulated with a non-ionic surfactant such as Tween, polyethylene glycol or glycerine. Thus, the compounds and their physiologically acceptable solvates may be formulated for administration by inhalation or insufflation (either through the mouth or the nose) or oral, buccal, parenteral, topical, dermal, vaginal, rectal administration and drug delivery device, e.g., porous or viscous material, such as lipofoam.

For oral administration, the pharmaceutical preparation may be in liquid form, for example, solutions, syrups or suspensions, or may be presented as a drug product for reconstitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, or fractionated vegetable oils); and preservatives (e.g., methyl or propyl-p-hydroxybenzoates or sorbic acid). The pharmaceutical compositions may take the form of, for example, tablets or capsules prepared by conventional means with pharmaceutically acceptable excipients such as binding agents (e.g., pregelatinized maize starch, polyvinyl pyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well-known in the art.

Preparations for oral administration may be suitably formulated to give controlled release of the active compound.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The antibiotic compounds may also be formulated in rectal compositions such as suppositories or retention enemas, e.g., containing conventional suppository bases such as cocoa butter or other glycerides.

In addition to the formulations described previously, the antibiotic compounds may also be formulated as a depot preparation. Such long acting formulations may be administered by implantation (for example, subcutaneously or intramuscularly) or by intramuscular injection. Thus, for example, the antibiotic compounds may be formulated with suitable polymeric or hydrophobic materials (for example, as an emulsion in an acceptable oil) or ion exchange resins, or as sparingly soluble derivatives, for example, as a sparingly soluble salt. Liposomes and emulsions are well known examples of delivery vehicles or carriers for hydrophilic drugs.

The antibiotic compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

The pharmaceutical compositions of the present invention comprise an antibiotic compound as the active ingredient, or a pharmaceutically acceptable salt thereof, and may also contain a pharmaceutically acceptable carrier, and optionally, other therapeutic ingredients, for example antivirals. The term "pharmaceutically acceptable salts" refers to salts prepared from pharmaceutically acceptable non-toxic acids and bases, including inorganic and organic acids and bases.

The pharmaceutical compositions include compositions suitable for oral, rectal, mucosal routes, transdermal, parenteral (including subcutaneous, intramuscular, intrathecal and intravenous), although the most suitable route in any given case will depend on the nature and severity of the condition being treated.

In practical use, an antibiotic agent can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including tablets, capsules, powders, intravenous injections or infusions). In preparing the compositions for oral dosage form any of the usual pharmaceutical media may be employed, e.g., water, glycols, oils, alcohols, flavoring agents, preservatives, coloring agents, and the like; in the case of oral liquid preparations, e.g., suspensions, solutions, elixirs, liposomes and aerosols; starches, sugars, microcrystalline cellulose, diluents, granulating agents, lubricants, binders, disintegrating agents, and the like in the case of oral solid preparations e.g., powders, capsules, and tablets. In preparing the compositions for parenteral dosage form, such as intravenous injection or infusion, similar pharmaceutical media may be employed, e.g., water, glycols, oils, buffers, sugar, preservatives and the like know to those skilled in the art. Examples of such parenteral compositions include, but are not limited to Dextrose 5% w/v, normal saline or other solutions.

5.10.2. ADMINISTRATION

For administration to subjects, antibiotic compounds discovered by using the assays of the invention are formulated in pharmaceutically acceptable compositions. The compositions can be used alone or in combination with one another, or in combination with other therapeutic or diagnostic agents. These compositions can be utilized in vivo, ordinarily in a mammal, preferably in a human, or in vitro. In employing them in vivo, the compositions can be administered to the mammal in a variety of ways, including parenterally, intravenously, subcutaneously, intramuscularly, colonially, rectally, vaginally, nasally, orally, transdermally, topically, ocularly, or intraperitoneally.

As will be readily apparent to one skilled in the art, the magnitude of a therapeutic dose of an antibiotic compound in the acute or chronic management of an infectious disease will vary with the severity of the condition to be treated, the particular composition employed, and the route of administration. The dose, and perhaps dose frequency, will also vary according to the species of the animal, the age, body weight, condition and response of the individual subject. The determination of effective dosage levels, that is the dosage levels necessary to achieve the desired result, will be within the ambit of one skilled in the art.

Desirable blood levels may be maintained by a continuous infusion of an antibiotic compound as ascertained by plasma levels. It should be noted that the attending physician would know how to and when to terminate, interrupt or adjust therapy to lower dosage due to toxicity. Conversely, the attending physician would also know how to and when to adjust treatment to higher levels if the clinical response is not adequate (precluding toxic side effects).

In selected cases, drug delivery vehicles may be employed for systemic or topical administration. They can be designated to serve as a slow release reservoir, or to deliver their contents directly to the target cell. Such vehicles have been shown to also increase the circulation half-life of drugs which would otherwise be rapidly cleared from the blood stream. Some examples of such specialized drug delivery vehicles which fall into this category are liposomes, hydrogels, cyclodextrins, and bioadhesive microspheres. These vehicles have been developed for chemotherapeutic agents.

Topical administration of agents is advantageous when localized concentration at the site of administration with minimal systemic adsorption is desired. This simplifies the delivery strategy of the agent to the disease site and reduces the extent of toxicological characterization. Furthermore, the amount of material to be administered is far less than that required for other administration routes.

Antibiotic agents may also be systemically administered. Systemic absorption refers to the accumulation of agents in the blood stream followed by distribution throughout the entire body. Administration routes which lead to systemic absorption include: oral, intravenous, subcutaneous, intraperitoneal, intranasal, intrathecal and ocular. Each of these administration routes exposes the agent to an accessible target.

5.10.3. TARGET INFECTIOUS AGENTS

The antibiotic compounds identified by the methods of the infection can be used to treat infectious diseases in animals, including humans, companion animals (e.g., dogs and cats), livestock animals (e.g., sheep, cattle, goats, pigs, and horses), laboratory animals (e.g., mice, rats, and rabbits), and captive or wild animals.

Specifically, infectious diseases caused by bacteria including but not limited to, gram positive cocci, such as Staphylococci (e.g., *S. aureus*), Streptococci (e.g., *S. pneumoniae, S. pyrogens, S. faecalis, S. viridans*); gram positive bacilli, such as Bacillus (e.g., *B. anthracis*), Corynebacterium (e.g., *C. diphtheriae*), Listeria (e.g., *L. monocytogenes*); gram negative cocci, such as Neisseria (e.g., *N. gonorrhoeae, N. Meningitidis*); gram negative bacilli, such as Haemophilus (e.g. *H. influenzae*), Pasteurella (e.g., *P. multocida*), Proteus (e.g., *P. mirabilis*), Salmonella (e.g., *S. typhi murium*), Shigella species, Escherichia (e.g., *E. coli*), Klebsiella (e.g., *K. pneumoniae*), Serratia (e.g. *S. marcescens*), Yersinia (e.g., *Y. pestis*), Providencia species, Enterobacter species, Bacteroides (e.g., *fragilis*), Acinetobacter species, Campylobacter (e.g., *C. jejuni*), Pseudomonas (e.g., *P. aeruginosa*), Bordetella (e.g., *B. pertussis*), Brucella species, Fracisella (e.g., *F. tularensis*), Clostridia (e.g., *C. perfriugens*), Helicobacter (e.g., *H. pylori*), Vibrio (e.g., *V. cholerae*), Mycoplasma (e.g., *M. pneumoniae*), Legionella (e.g., *L. pneumophila*), Spirochetes (e.g. Treponema, Leptospira and Borrelia), Mycobacteria (e.g., *M. tuberculosis*), Nocardia (e.g., *N. asteroides*), Chlamydia (e.g., *C. trachomatis*), and Rickettsia species, can be treated by antibiotic drugs discovered by the methods of the invention.

6. EXAMPLES

6.1.1. SCREENING ASSAY USING AN *E. coli* STRAIN WITH A REPORTER GENE NEGATIVELY REGULATED BY ppGpp

6.1.1. INOCULATION OF LB (LURIA BROTH) WITH *E. coli* STRAIN VH2736

LB (Luria Broth) prepared as described in Maniatis, et al., supra, Section 5.4.3, was inoculated with the *E. coli* strain VH2736 by removing *E. coli* VH2736 glycerol stock from −70° C. freezer, scraping off a loopful of frozen culture with a sterile inoculating loop, and streaking onto a LB agar plate (+50 μg/ml kanamycin) that had been warmed to room temperature. The plate was incubated at 37° C. for 18–24 hours. Five single, isolated colonies were selected from the plate. 25 mL of LB (+50 μg/ml of kanamycin) was then added with a sterile pipet to an autoclaved 125 mL Erlenmeyer flask. Using a sterile loop, the selected colonies were transferred from the plate to the LB master flask. The flask was incubated at 37° C. while shaking for 16–18 hrs. at 250 rpm. The LB plate with culture is stored at 2–8° C.

6.1.2. DILUTION OF OVERNIGHT CULTURE

The Erlenmeyer flask was removed from the 37° C. incubator and using LB broth as a reference, the optical density (OD) of a 1:10 dilution of the culture (dilute with LB broth) was determined, using a spectrophotometer set at 460 nm wavelength light and a 1 cm path length. The turbidity of the culture at 16–18 hours should be around 4.500–5.000 OD units at 460 nm. When the OD was appropriate, a 1:5000 dilution of the culture with 1× Minimal medium (as described in Maniatis et al., MOLECULAR CLONING A Laboratory Manual, Cold Spring Harbor Press, eds. 1982) containing 50 μg/ml of kanamycin was made.

6.1.3. INOCULATION OF LACTOSE-TETRAZOLIUM PLATES 16 ml of the 1:5000 dilution was pipetted and added directly to the surface of a 10×10 inch plate containing lactose-tetrazolium medium (as described in Silhavey et al., Experiments with Gene Fusions, Cold Spring Harbor Press, 1984, ppGpp. 268–9). The lactose-tetrazolium plate contained approximately 300 ml of medium in a square plaque tray (Stratagene, Inc.). The medium contained 25.5 g BBL-Base, antibiotic medium 2(Becton Dickinson Microbiology Systems) 50 mg 2,3,5-triphenyl-2H tetrazolium chloride and 50 ml 20% beta-lactose solution per liter. The plate was swirled slowly to cover the entire surface evenly with the diluted culture. After the culture covered the agar plate surface, the plate was tipped diagonally so that the remaining liquid accumulated in one corner. Using a sterile pipet, the remaining liquid was removed from the plate. The plate was then placed, lid off, in a laminar flow hood to dry for 2 hours.

6.1.4. ADDITION OF COMPOUNDS

3 μl of each test compound from four 96-well plates were added to one assay plate. The assay plates had been previously stamped by a 96-pin stamp which created holes in the agar surface with an automated pipetting machine (Microlab 2200 Automated Pipetting System, Hamilton Co.). An additional row of wells were added in the center of the plate for dilutions of known positive and negative compounds. The following controls were added:

| | |
|---|---|
| positive controls: | phenanthroline, 10 mg/ml |
| | polymyxin E, 10 mg/ml |
| negative controls: | spectinomycin, 10 mg/ml |
| | tetracycline, 1 mg/ml |

The cells were incubated at 37° C. for 24 hours.

6.1.5. SELECTION OF POSITIVE COMPOUNDS

A positive result was indicated by a red ring of growth around the well.

6.2. SCREENING FOR COMPOUNDS WHICH CAUSE ppGpp ACCUMULATION VIA AN *E. COLI* STRAIN POSITIVELY REGULATED BY ppGpp

The test compounds which yielded a positive result was then "retested" using a strain of *E. coli* hisP$_1$lacZ (relA$^-$, spoT$^+$) which contains the reporter lacZ gene under the control of positive promotor, the hisP, promoter.

6.2.1. INOCULATION OF LB (LURIA BROTH) WITH *E. coli* hisP$_1$lacZ (relA$^-$,spoT$^+$)

LB (Luria Broth) prepared as described in Maniatis, et al., supra, Section 5.4.3, was inoculated with the *E. coli* strain hisP$_1$lacZ (relA$^-$, spoT$^+$) by removing *E. coli* hisP$_1$lacZ (relA$^-$, spoT$^+$) glycerol stock from −70° C. freezer, scraping off a loopful of frozen culture with a sterile inoculating loop, and streaking onto a LB agar plate that had been warmed to room temperature. The plate was incubated at 37° C. for 18–24 hours. Five single, isolated colonies were selected from the plate. 25 mL of LB was then added with a sterile pipet to an autoclaved 150 mL Erienmeyer flask. 125 μl of sterile 40% dextrose solution was also added to the flask. Using a sterile loop, the selected colonies were transferred from the plate to the LB flask. The flask was incubated at 37° C. while shaking for 16–18 hrs. at 250 rpm. The LB master plate with culture is stored at 2–8° C.

6.2.2. DILUTION OF OVERNIGHT CULTURE

The Erlenmeyer flask was removed from 37° C. incubator and using LB broth as a reference, the OD of a 1:10 dilution of the culture (dilute with LB broth) was checked. The turbidity of the culture at 16–18 hours should be around 4.500–5.000. When the OD was appropriate, a 1:5000 dilution of the culture with 1× Minimal media was made.

6.2.3. INOCULATION OF X-GAL PLATES 16 ml of the 1:5000 dilution was pipetted and added directly to the surface of the X-Gal plate (LB agar plate with 80 μg/ml X-gal). The x-gal plate contained approximately 300 ml of medium in a square plaque tray (Stratagene, Inc.). The plate was swirled slowly to cover the entire surface evenly with the diluted culture. After the culture covered the agar plate surface, the plate was tipped diagonally so that the remaining liquid accumulated in one corner. Using a sterile pipet, the remaining liquid was removed from the plate. The plate was then placed, lid off, in a laminar flow hood to dry for 1 hour.

6.2.4. ADDITION OF COMPOUNDS

3 μl of each test compound from four 96-well plates which yielded a positive result in Section 6.1 were added to one assay plate. The assay plates had been previously stamped by a 96-pin stamp which created holes in the agar surface with an automated pipetting machine (Microlab 2200 Automated Pipetting System, Hamilton Co.). An additional row of wells were added in the center of the plate for dilutions of known positive and negative compounds. The following controls were added:

| | |
|---|---|
| positive controls: | phenanthroline, 10 mg/ml |
| | polymyxin E, 10 mg/ml |
| negative controls: | spectinomycin, 10 mg/ml |
| | tetracycline, 1 mg/ml |

The cells were incubated at 37° C. for 24 hours.

6.2.5. SELECTION OF POSITIVE COMPOUNDS

Like the positive controls, a positive result was indicated by a compound with a dark blue ring of growth surrounding a zone of growth inhibition. Negative controls had zones of inhibition but no dark rings of growth.

6.3. TLC ANALYSIS

After getting a positive result in the second assay described in Section 6.2. TLC analysis was performed as described in Section 5.6. The results indicated that both phenanthroline and the "positive" agent from the assay in Section 6.2 gave positive results. By positive results is meant accumulation of ppGpp in excess of control reactions without added compound.

7. DEPOSIT OF MICROORGANISMS

The following microorganism was deposited with the American Type Culture Collection (ATCC), 10801 University Blvd, Manassas, Va. on Feb. 10, 1998 and assigned the indicated accession number:

| Microorganism | ATCC Accession No. |
|---|---|
| E. coli, VH2736 | 202090 |

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

Various publications are cited herein, the disclosures of which are incorporated by reference in their entireties.

What is claimed:

1. A method for screening for test compounds that cause ppGpp accumulation in bacteria comprising:
   (a) contacting a relA deficient test cell under a stress condition with a test compound for a time sufficient to allow the test compound to cause ppGpp accumulation in the test cell; and
   (b) detecting growth of the test cell under the stress condition, wherein an increase in growth of the test cell contacted with the test compound relative to the growth of the test cell not contacted with the test compound, indicates that the test compound causes ppGpp accumulation in the test cell.

2. A method for screening for test compounds that cause ppGpp accumulation in bacteria comprising:
   (a) contacting a relA deficient test cell with a test compound for a time sufficient to allow the test compound to cause ppGpp accumulation in the test cell, wherein the test cell contains a reporter gene operably linked to a promoter which is negatively regulated by ppGpp, and
   (b) detecting the expression of the reporter gene in the test cell, wherein a decrease in the expression of the reporter gene in the test cell contacted with the test compound relative to the expression of the reporter gene in a test cell not contacted with the test compound, indicates that the test compound causes ppGpp accumulation in the test cell.

3. A method for screening for test compounds that cause ppGpp accumulation in bacteria comprising:
   (a) contacting a relA deficient test cell with a test compound for a time sufficient to allow the test compound to cause ppGpp accumulation in the test cell, wherein the test cell contains a reporter gene operably linked to a promoter which is positively regulated by ppGpp, and
   (b) detecting the expression of the reporter gene in the test cell, wherein an increase in the expression of the reporter in the test cell contacted with the test compound relative to the expression of the reporter gene in a test cell not contacted with the test compound, indicates that the test compound causes ppGpp accumulation in the test cell.

4. The method of claim 1 wherein the test cell further comprises a wildtype spoT$^+$ locus.

5. The method of claim 2 wherein the test cell further comprises a wildtype spoT$^+$ locus.

6. The method of claim 3 wherein the test cell further comprises a wildtype spoT$^+$ locus.

7. The method of claim 4, 5, or 6 wherein the test compound causes ppGpp accumulation in the test cell by enhancing ppGpp synthase II activity, or by inhibiting ppGpp degradase activity.

8. The method of claim 4 wherein the test cell is an E. coli.

9. The method of claim 5 wherein the test cell is an E. coli.

10. The method of claim 6 wherein the test cell is an E. coli.

11. The method of claim 1 or 8 wherein the stress condition is caused by amino acid starvation.

12. The method of claim 1 or 8 wherein the stress condition is caused by culturing the test cell in minimal media containing 3-amino-1,2,4-triazol.

13. The method of claim 1 or 8 wherein the stress condition is caused by culturing the test cell in minimal media containing serine hydroxymate.

14. The method of claim 2 or 9 wherein the reporter gene is operably associated with a promoter of a ribosomal RNA-encoding gene.

15. The method of claim 14 wherein the reporter gene is operably associated with the rrnBP1 promoter.

16. The method of claim 15 wherein the reporter gene is the E. coli β-galactosidase gene.

17. The method of claim 15 wherein the test cell is cultured in a rich media comprising (i) lactose and 2,3,5-triphenyl-2H-tetrazolium, or (ii) 5-bromo-4-chloro-3-indolyl-β-D-galactoside.

18. The method of claim 3 or 10 wherein the reporter gene is operably associated with a promoter for histidine biosynthesis.

19. The method of claim 18 wherein the reporter gene is operably associated with the hisp1 promoter or hisP2 promoter.

20. The method of claim 18 wherein the reporter gene is the E. coli β-galactosidase gene.

21. The method of claim 18 wherein the test cell is cultured in a rich media comprising (i) lactose and 2,3,5-triphenyl-2H-tetrazolium, or (ii) 5-bromo-4-chloro-3-indolyl-β-D-galactoside.

22. The method of claim 17 wherein the test cell is E. coli strain VH2736.

23. A method for screening for test compounds that cause ppGpp accumulation in bacteria comprising:
   (a) culturing E. coli strain VH2736 test cells;
   (b) inoculating a plate containing a medium comprising lactose and 2,3,5-triphenyl-2H-tetrazolium with the test cells;
   (c) adding a test compound to a point of application in the plate and incubating the plate for a time sufficient to allow the test compound to contact the test cell and cause ppGpp accumulation;
   (d) detecting a red coloration and growth of the test cells contacted with the test compound, wherein the red coloration indicates a lack of expression of the β-galactosidase gene in the test cells; and
   (e) comparing the coloration and growth of test cells not contacted with the test compound;
wherein an increase in red coloration and growth of the test cell contacted with the test compound relative to the coloration and growth of test cells not contacted with the test compound indicates that the test compound causes ppGpp accumulation in the test cell.

24. A method for screening for test compounds that cause ppGpp accumulation in bacteria comprising:
   (a) culturing a relA deficient strain of E. coli test cell wherein the test cells contains a β-galactosidase gene operably linked to a promoter which is positively regulated by ppGpp;
   (b) inoculating a plate containing a medium comprising 5-bromo-4-chloro-3-indolyl-β-D-galactoside with the test cells;
   (c) adding a test compound to a point of application in the plate and incubating the plate for a time sufficient to allow the test compound to contact the test cell and cause ppGpp accumulation;
   (d) detecting a blue coloration and an inhibition of growth of the test cells contacted with the test compound, wherein the blue coloration indicates expression of the β-galactosidase gene in the test cells; and
   (e) comparing the coloration and growth of test cells not contacted with the test compound;
wherein an increase in blue coloration, and an inhibition of growth of the test cell contacted with the test compound relative to the coloration and growth of test cells not contacted with the test compound indicates that the test compound causes ppGpp accumulation in the test cell.

25. A method for screening for test compounds that cause ppGpp accumulation in bacteria comprising:
   (a) contacting a relA$^+$ test cell under a non-stress condition so that ppGpp synthetase I is inactive with a test compound for a time sufficient to allow the test compound to cause ppGpp accumulation in the test cell, wherein the test cell contains a reporter gene operably linked to a promoter which is negatively regulated by ppGpp, and
   (b) detecting the expression of the reporter gene in the test cell, wherein a decrease in the expression of the reporter gene in the test cell contacted with the test compound relative to the expression of the reporter gene in a test cell not contacted with the test compound, indicates that the test compound causes ppGpp accumulation in the test cell.

26. A method for screening for test compounds that cause ppGpp accumulation in bacteria comprising:
   (a) contacting a relA$^+$ test cell under a non-stress condition so that ppGpp synthetase I is inactive with a test compound for a time sufficient to allow the test compound to cause ppGpp accumulation in the test cell, wherein the test cell contains a reporter gene operably linked to a promoter which is positively regulated by ppGpp, and
   (b) detecting the expression of the reporter gene in the test cell, wherein an increase in the expression of the reporter in the test cell contacted with the test compound relative to the expression of the reporter gene in a test cell not contacted with the test compound, indicates that the test compound causes ppGpp accumulation in the test cell.

* * * * *